United States Patent
Carreño Serraïma et al.

(10) Patent No.: US 8,815,266 B2
(45) Date of Patent: Aug. 26, 2014

(54) PEPTIDE DERIVATIVES USEFUL IN THE TREATMENT, CARE OR CLEANSING OF THE SKIN, MUCOSAE, SCALP OR NAILS

(75) Inventors: Cristina Carreño Serraïma, Barcelona (ES); Wim Van Den Nest, Barcelona (ES); Ana Sempere Bonete, Elche-Alicante (ES); Antonio Ferrer Montiel, Alicante (ES); Juan Cebrián Puche, Barcelona (ES); Nuria Almiñana Doménech, Barcelona (ES); David Panyella Costa, Barcelona (ES); José Ginestar González, Toulouse (FR)

(73) Assignees: Lipotech, S.A., Gava-Barcelona (ES); Diverdrugs, S.L, Gava-Barcelona (ES); Puig, S.A., Barcelona (ES)

( * ) Notice: Subject to any disclaimer, the term of this patent is extended or adjusted under 35 U.S.C. 154(b) by 146 days.

(21) Appl. No.: 12/865,311

(22) PCT Filed: Jan. 30, 2009

(86) PCT No.: PCT/EP2009/051041
§ 371 (c)(1),
(2), (4) Date: Nov. 17, 2010

(87) PCT Pub. No.: WO2009/095456
PCT Pub. Date: Aug. 6, 2009

(65) Prior Publication Data
US 2011/0052519 A1     Mar. 3, 2011

Related U.S. Application Data

(60) Provisional application No. 61/039,599, filed on Mar. 26, 2008.

(30) Foreign Application Priority Data

Jan. 30, 2008 (ES) .................................. 200800243

(51) Int. Cl.
| | | |
|---|---|---|
| *A61K 8/64* | (2006.01) |
| *A61K 38/06* | (2006.01) |
| *A61K 38/07* | (2006.01) |
| *C07K 5/09* | (2006.01) |
| *C07K 5/093* | (2006.01) |
| *C07K 5/11* | (2006.01) |
| *C07K 5/113* | (2006.01) |
| *A61Q 19/00* | (2006.01) |
| *A61K 38/00* | (2006.01) |
| *A61Q 3/00* | (2006.01) |
| *A61Q 11/00* | (2006.01) |
| *A61Q 5/00* | (2006.01) |

(52) U.S. Cl.
CPC .............. *C07K 5/1019* (2013.01); *A61Q 19/00* (2013.01); *A61K 38/00* (2013.01); *A61Q 3/00* (2013.01); *C07K 5/0819* (2013.01); *C07K 5/0817* (2013.01); *A61Q 11/00* (2013.01); *A61K 8/64* (2013.01); *C07K 5/1021* (2013.01); *A61Q 5/00* (2013.01)
USPC ............ 424/401; 424/61; 424/69; 424/70.14; 514/2.3; 514/2.4; 514/21.9; 530/330; 530/331

(58) Field of Classification Search
None
See application file for complete search history.

(56) References Cited

U.S. PATENT DOCUMENTS

| 6,974,799 B2* | 12/2005 | Lintner ........................ 514/18.8 |
| 2004/0259795 A1* | 12/2004 | Julius et al. ..................... 514/12 |
| 2007/0185025 A1* | 8/2007 | Palacios et al. ................. 514/12 |

FOREIGN PATENT DOCUMENTS

| GB | 2166139 A * | 4/1986 |
| WO | WO 2004055041 A2 * | 7/2004 |

OTHER PUBLICATIONS

International Search Report issued by the International Searching Authority (ISA/O.E.P.M.) on Jun. 10, 2009 in connection with International Application No. PCT/ES2009/051041.

* cited by examiner

*Primary Examiner* — Jeffrey E Russel
(74) *Attorney, Agent, or Firm* — Fay Sharpe LLP

(57) ABSTRACT

The invention relates to peptide derivatives of general formula (I):

$$R^1\text{-}AA^1\text{-}AA^2\text{-}R^3\text{-}AA^4\text{-}R^2 \qquad (I)$$

their stereoisomers, mixtures thereof, and their cosmetically or pharmaceutically acceptable salts, a method for obtaining them, cosmetic or pharmaceutical compositions containing them and their use for the treatment, care and/or cleansing of those conditions, disorders and/or pathologies of the skin, mucosae, scalp and/or nails resulting from microorganism proliferation or being at risk of microorganism proliferation.

24 Claims, No Drawings

SEQUENCE LISTING

```
<160> NUMBER OF SEQ ID NOS: 28

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Phg

<400> SEQUENCE: 1

Arg Xaa Ala Ile
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Ahx
<220> FEATURE:
<221> NAME/KEY: MISC_FEATURE
<222> LOCATION: (3)..(3)
<223> OTHER INFORMATION: Xaa is Phg

<400> SEQUENCE: 2

Arg Xaa Xaa Ile
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Glu Met Ala Ile
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (3)..(3)
<223> OTHER INFORMATION: Xaa is Phg

<400> SEQUENCE: 4

Arg Met Xaa Ile
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Phg

<400> SEQUENCE: 5

Glu Xaa Ala Ile
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Phg

<400> SEQUENCE: 6

Glu Met Xaa Ile
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Ahx

<400> SEQUENCE: 7

Arg Xaa Ala Ile
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Phg
<220> FEATURE:
<221> NAME/KEY: MISC_FEATURE
<222> LOCATION: (3)..(3)
<223> OTHER INFORMATION: Xaa is Phg

<400> SEQUENCE: 8

Arg Xaa Xaa Ile
```

```
<210> SEQ ID NO 9
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Phg
<220> FEATURE:
<221> NAME/KEY: MISC_FEATURE
<222> LOCATION: (3)..(3)
<223> OTHER INFORMATION: Xaa is Phg

<400> SEQUENCE: 9

Glu Xaa Xaa Ile
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Arg Met Ala Ile
1

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is L-Phg

<400> SEQUENCE: 11

Arg Xaa Ala Ile
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is D-Phg

<400> SEQUENCE: 12

Arg Xaa Ala Ile
1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (2)..(2)
<223> OTHER INFORMATION: Xaa is Ahx
<220> FEATURE:
<221> NAME/KEY: MISC_FEATURE
<222> LOCATION: (3)..(3)
<223> OTHER INFORMATION: Xaa is L-Phg

<400> SEQUENCE: 13

Arg Xaa Xaa Ile
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Ahx
<220> FEATURE:
<221> NAME/KEY: MISC_FEATURE
<222> LOCATION: (3)..(3)
<223> OTHER INFORMATION: Xaa is D-Phg

<400> SEQUENCE: 14

Arg Xaa Xaa Ile
1

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is L-Phg

<400> SEQUENCE: 15

Arg Met Xaa Ile
1

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is D-Phg

<400> SEQUENCE: 16

Arg Met Xaa Ile
1

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is L-Phg
```

```
<400> SEQUENCE: 17

Glu Xaa Ala Ile
1

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is D-Phg

<400> SEQUENCE: 18

Glu Xaa Ala Ile
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is L-Phg

<400> SEQUENCE: 19

Glu Met Xaa Ile
1

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is D-Phg

<400> SEQUENCE: 20

Glu Met Xaa Ile
1

<210> SEQ ID NO 21
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is L-Phg
<220> FEATURE:
<221> NAME/KEY: MISC_FEATURE
<222> LOCATION: (3)..(3)
<223> OTHER INFORMATION: Xaa is L-Phg

<400> SEQUENCE: 21

Arg Xaa Xaa Ile
1

<210> SEQ ID NO 22
```

```
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is L-Phg
<220> FEATURE:
<221> NAME/KEY: MISC_FEATURE
<222> LOCATION: (3)..(3)
<223> OTHER INFORMATION: Xaa is D-Phg

<400> SEQUENCE: 22

Arg Xaa Xaa Ile
1

<210> SEQ ID NO 23
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is D-Phg
<220> FEATURE:
<221> NAME/KEY: MISC_FEATURE
<222> LOCATION: (3)..(3)
<223> OTHER INFORMATION: Xaa is L-Phg

<400> SEQUENCE: 23

Arg Xaa Xaa Ile
1

<210> SEQ ID NO 24
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is D-Phg
<220> FEATURE:
<221> NAME/KEY: MISC_FEATURE
<222> LOCATION: (3)..(3)
<223> OTHER INFORMATION: Xaa is D-Phg

<400> SEQUENCE: 24

Arg Xaa Xaa Ile
1

<210> SEQ ID NO 25
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is L-Phg
<220> FEATURE:
<221> NAME/KEY: MISC_FEATURE
<222> LOCATION: (3)..(3)
<223> OTHER INFORMATION: Xaa is L-Phg

<400> SEQUENCE: 25
```

```
Glu Xaa Xaa Ile
1

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is L-Phg
<220> FEATURE:
<221> NAME/KEY: MISC_FEATURE
<222> LOCATION: (3)..(3)
<223> OTHER INFORMATION: Xaa is D-Phg

<400> SEQUENCE: 26

Glu Xaa Xaa Ile
1

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is D-Phg
<220> FEATURE:
<221> NAME/KEY: MISC_FEATURE
<222> LOCATION: (3)..(3)
<223> OTHER INFORMATION: Xaa is L-Phg

<400> SEQUENCE: 27

Glu Xaa Xaa Ile
1

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is D-Phg
<220> FEATURE:
<221> NAME/KEY: MISC_FEATURE
<222> LOCATION: (3)..(3)
<223> OTHER INFORMATION: Xaa is D-Phg

<400> SEQUENCE: 28

Glu Xaa Xaa Ile
1
```

PEPTIDE DERIVATIVES USEFUL IN THE TREATMENT, CARE OR CLEANSING OF THE SKIN, MUCOSAE, SCALP OR NAILS

The application is a §371 national stage of PCT International Application No. PCT/EP2009/051041, filed Jan. 30, 2009, claiming priority of U.S. Provisional Application No. 61/039,599, filed Mar. 26, 2008 and Spanish Patent Application No. P200800243.8, filed Jan. 30, 2008, the contents of all of which are hereby incorporated by reference into this application.

FIELD OF THE INVENTION

The present invention relates to peptide derivatives capable of stimulating the production of endogenous β-defensins and to cosmetic and/or pharmaceutical compositions containing these peptide derivatives for the treatment, care and/or cleansing of the skin, mucosae, scalp and/or nails, preferably for the treatment of those conditions, disorders and/or pathologies of the skin, mucosae, scalp and/or nails resulting from microorganism proliferation or being at risk of microorganism proliferation.

BACKGROUND OF THE INVENTION

The skin of mammals is their main defense barrier against external aggressions, whether they are chemical, mechanical or infectious aggressions. External aggressive agents also include environmental factors such as UV rays, tobacco smoke, pollution and climate. The skin has a cutaneous microbial flora forming its immune protection system; any unbalance in the population of said flora entails a functional immune deficit which often involves the invasion of the skin by autochthonous skin bacteria or by bacteria that are not usually in the skin, a process thus commencing which can result in a clinically established infection. Likewise, skin flora has multiple important functions of homeostasis, defense against bacterial infections (by interference), lipid degradation and production of volatile components responsible for body odor.

For example, the microorganisms which live as saprophytes in the surface of human skin, in its cracks, flakes, stratum corneum and hair follicles, have an important protective role as an additional skin barrier to the surface corneum and lipid layers, which determine the permeability between the internal and external medium. This dermal flora is formed by resident and transient microorganisms, and are bacteria, fungi and parasites.

Resident microorganisms have the capacity to multiply and survive adhered to the surface and are dominant skin constituents; examples of them are *Corynebacterium bovis, C. mutissium, C. xerosis, C. hoffmani, Propionibacterium avidum, P. granulosum, Acinetobacter*, the yeast *Malassezia furfur, Pityrosporum ovale* and *P. orbiculares*, as well as some groups of the Candida family, such as *C. glabrata*. The saprophyte parasite which is located in hair follicles, *Demodex folliculorum*, can be pathogenic.

Transient skin flora is mainly represented by Gram-positive bacteria, such as group A *Streptococcus, Staphylococcus aureus* and of the *Neisseria* genus or fungal flora such as *Candida albicans*, which is considered pathogenic whenever it is isolated in the skin.

Normal skin flora can be modified by several environmental factors, such as moisture and temperature, age, sex and race, as skin characteristics vary among people, which favors the colonization and proliferation of certain groups of microorganisms. Skin colonization depends on particular characteristics of each topographic area of the body, and the predominance of certain groups of microorganisms also varies according to the latter. In the scalp, for example, there is mixed flora, with bacteria, fungi and parasites, such as *Pityrosporum ovale, Staphylococcus, Corynebacterium* and *Demodex folliculorum*. Different groups of microorganisms of the axillary and perianal region, vulva or interdigital spaces can thus be isolated.

When this microbiological barrier is weakened or destroyed, as in the case of eczemas, irritations or aggressive skin treatments, pathogenic microorganisms can colonize skin or even traverse it, thus escaping the non-specific defense mechanisms of the skin. Thus, the presence of cutaneous microbial flora provides the skin with a defense barrier against pathogenic microorganisms by a nutritional competition phenomenon and by the secretion of substances with enzymatic and/or bactericidal activity.

The proliferation of pathogenic microorganisms such as for example *Staphylococcus aureus, Streptopyogenes* or *Propionibacterium acnes* or some yeasts entails a deregulation of the cutaneous flora system and can lead to more severe disorders or pathologies in the skin, mucosae, scalp and/or nails such as eczemas, candidiasis, dermatitis, onychomycosis or dermatosis among others. Likewise, in wound healing processes there is always a risk of infection, because the defense mechanisms of the skin, mucosae, scalp and/or nails are reduced. Wounds can be a result of physical injuries such as for example cuts, abrasions, burns, irritations, scrapes or exposure to chemical agents among others, a result of surgical processes such as for example surgical incisions or skin grafts among others, as well as a result of pathologies and even chronic conditions such as for example diabetic ulcers or venous ulcers among others. In a wound, the amount of inoculum of pathogenic microorganism, the virulence of said pathogens and the defense mechanisms of the host will determine if the wound will develop an infection, such that during healing processes the treatment with bactericidal compounds or compounds stimulating the defenses of the host are therapeutically useful [Edlich, R. F., Kenney J. G., Morgan R. F., Nichter L. S., Friedman H. I. and Rodeheaver G. T. (1986) "*Antimicrobial treatment of minor soft tissue lacerations: a critical review*" Emerg. Med. Clin. of North Am. 4:561-80].

In the same way, the growth of pathogenic microorganisms, and specifically the proliferation of *Pseudomonas aeruginosa* can also affect ocular mucosae, leading to ocular infections which can produce corneal ulcers. The risk of ocular infections is enhanced not only by bad hygiene habits, especially of the hands, but also by the daily use of contact lenses [Buehler P. O., Schein O. D., Stamler J. F., Verdier D. D. and Katz J. (1992) "*The increased risk of ulcerative keratitis among disposable soft contact lens users*" Arch. Ophthalmol. 110:1555-1558; Wilhelmus K. R. (1987) "*Review of clinical experience with microbial keratitis associated with contact lenses*" CLAO J. 13:211-214].

Some people have a specific risk of contracting infections in the skin, mucosae, scalp and/or nails because they have a suppressed immune system, such as for example AIDS patients or those people who are undergoing a chemotherapy or radiotherapy treatment due to cancerous processes [Epstein J. B. and Chow A. W. (1999) "*Oral complications associated with immunosuppression and cancer therapies*" Infect. Dis. Clin. North Am. 13:901-23]. In the same way, those people in stressful situations often have a suppressed immune system making them susceptible to contracting infections in the skin, mucosae, scalp and/or nails [Biondi M. and Zannino L. G. (1997) *"Psychological stress, neuroimmunomodulation, and susceptibility to infectious diseases in animals and man: a review"* Psychother Psychosom. 66:3-26].

Bromhidrosis or fetid odor is a result of microorganism proliferation in the skin, especially in the areas of the skin with a high degree of perspiration such as the axillae, genitalia or feet [Leyden J. J., McGinley K. J., Holzle E., Labows J. N. and Kligman A. M. (1981) *"The microbiology of the human axilla and its relationship to axillary odor"* J. Invest. Dermatol. 77:413-6]. The characteristic and unpleasant odor of sweat is a result of the decomposition of sweat and moist skin by bacteria and yeasts, and the consequent release of malodorous substances such as for example steroids, and can be treated with compounds controlling or reducing the microbial population of the area in which perspiration occurs [Elsner P. (2006) *"Antimicrobials and the Skin Physiological and Pathological Flora"* Curr. Probl. Dermatol. 33:35-41].

Another result of microorganism proliferation in the oral cavity is halitosis or malodor of the mouth. 85%-90% of the origin of halitosis is in oral causes such as the periodontal conditions, dentures and badly adapted restorations or a deficient dental hygiene. The microflora of the dorsal surface of the tongue and mostly Gram-negative anaerobic bacteria decompose food remains between teeth, remains of cells of the oral mucosa or of blood or of saliva, producing volatile substances such as simple fatty acids such as butyric acid, propionic acid or valeric acid and sulfurous components such as methyl mercaptan or hydrogen sulfide, or protein derivatives such as putrescine and cadaverine. The microorganisms causing halitosis include *Treponema denticola, Prevotella intermedia, Porphyromonas gingivalis, Bacteroides forsythus, Fusobacterium periodonticum* or *Stomatococcus mucilaginus* among others [De Boever E. H. and Loesche W. J. (1995) *"Assessing the contribution of anaerobic microflora of the tongue to oral malodor"* J. Am. Dent. Assoc. 126:1384-1393; De Boever E. H., De Uzeda M. and Loesche W. J. (1994) *"Relationship between volatile sulfur compounds, BANA-hydrolyzing bacteria and gingival health in patients with and without complaints of oral malodor"* J. Clin. Dent. 4:114-119; Kozlovsky A., Gordon D., Gelernter I., Loesche W. J. and Rosenberg M. (1994) *"Correlation between the BANA test and oral malodor parameters"* J. Dent. Res. 73:1036-1042]. To control the malodor of buccal origin the treatment must be aimed towards the elimination of these microorganisms, whereby compounds controlling or reducing the microbial population of the buccal area will be useful in the treatment of halitosis.

Likewise, pathogenic microorganism proliferation can be reinforced by the reduction of the natural defense systems of mammals, and specifically by the reduction of defensin expression, defensins being specific proteins against infections which are located in the skin and in mucosae.

Defensins are a class of natural antimicrobial peptides present in plants, insects and in different mammals, including human beings. They are small molecules of about 30-40 amino acids, having in common a large number of positively charged amino acids such as arginine, as well as the presence of cysteine residues forming disulfide bonds conferring them their three-dimensional structure containing a set of antiparallel β sheets as a motif [Martin E., Ganz T. and Lehrer R. I. (1995) *"Defensins and other endogenous peptide antibiotics of vertebrates"* J. Leukocyte Biol. 58:128-133; Ganz T. and Lehrer R. I. (1994) *"Defensins"* Curr. Opinion Immunol. 6:584-589].

In mammals, defensins are classified into two families, according to the pattern of disulfide bonds that they have [Harder J., Bartels J., Christophers E. and Schröder J. M. (2001) *"Isolation and characterization of human β-defensin-3, a novel inducible peptide antibiotic"* J. Biol. Chem. 276: 5707-5713]. In the case of human beings, α-defensins or HNPs have three disulfide bonds between the cysteine residues $Cys^1$-$Cys^6$, $Cys^2$-$Cys^4$ and $Cys^3$-$Cys^5$, and are located in neutrophils (HNP1 to HNP4) and in the gastrointestinal apparatus (HNP5 and HNP6). Human β-defensins or hBDs have three disulfide bonds between the cysteine residues $Cys^1$-$Cys^5$, $Cys^2$-$Cys^4$ and $Cys^3$-$Cys^6$, they are constitutively expressed in keratinocytes and are located in the kidney, pancreas, saliva, lungs, placenta and skin (hBD1), in the skin, trachea and lungs (hBD2), in the skin, trachea, tonsils and tongue (hBD3) and in the testicles and stomach (hBD4).

hBD2 and hBD3 are the only human defensins which are inducible and are regulated at transcriptional level in response to the contact with microorganisms. These hBDs are overexpressed by differentiated keratinocytes in those places in which an inflammation and/or an infection occurs [Harder J., Bartels J., Christophers E. and Schröder J. M. (1997) *"A peptide antibiotic from human skin"* Nature 387:861]. The mechanism of action proposed for hBD2 is the binding to the target bacteria and its subsequent insertion in the lipid membrane of the microbe, altering the permeability of the membrane and therefore its internal homeostasis. hBD2 is highly effective killing Gram-negative bacteria, whereas it only has bacteriostatic activity against Gram-positive bacteria. The spectrum of hBD3 is broader than that of hBD2 and is effective as a bactericide against different Gram-positive and Gram-negative bacteria [Harder J., Bartels J., Christophers E. and Schröder J. M. (2001) *"Isolation and characterization of human β-defensin-3, a novel inducible peptide antibiotic"* J. Biol. Chem. 276:5707-5713; Garcia J. R., Jaumann F., Schukz S., Krause A., Rodriguez-Jimenez J., Forssmann U., Adermann K., Kluver E., Vogelmeier C., Becker D., Hedrich R., Forssmann W. G. and Bals R. (2001) *"Identification of a novel, multifunctional β-defensin (human β-defensin 3) with specific antimicrobial activity. Its interaction with plasma membranes of Xenopus oocytes and the induction of macrophage chemoattraction"* Cell Tissue Res. 306:257-264].

There is a direct correlation between hBD expression and the incidence of infections in human beings. hBD1 and hBD2 are extensively expressed in oral inflammation tissue samples, as well as in primary oral keratinocytes [Harder J., Bartels J., Christophers E., and Schröder J. M. (2001) *"Isolation and characterization of human β-defensin-3, a novel inducible peptide antibiotic"* J. Biol. Chem. 276:5707-5713]. In addition, the skin of patients affected by psoriasis, in which epithelial hBDs are overexpressed, has relatively low infection statistics, whereas in patients with atopic dermatitis, in whom hBD expression is suppressed, injuries are easily infected [Nomura I., Goleva E., Howell M. D., Hamid Q. A., Ong P. Y., Hall C. F., Darse M. A., Gao B., Boguniewicz M., Travers J. B. and Leung D. Y. (2003) *"Cytokine milieu of atopic dermatitis, as compared to psoriasis, skin prevents induction of innate immune response genes"* J. Immunol. 171:3262-3269; Ong P. Y., Ohtake, T., Brandt C., Strickland I., Boguniewicz M., Ganz T., Gallo R. L. and Leung D. Y. (2002) *"Endogenous antimicrobial peptides and skin infections in atopic dermatitis"* N. Engl. J. Med. 347:1151-1160].

The pharmaceutical industry has focused its efforts on the development of a potent pharmacological collection of compounds with bactericidal and/or fungicidal activity to treat infections of the skin, mucosae, scalp and/or nails. Said treatments are not free of side-effects and further have the drawback that their continuous use leads to the resistance of pathogenic microorganisms against said compounds. It is therefore necessary to develop compounds which allow controlling pathogenic microorganism proliferation in the skin, mucosae, scalp and/or nails in a more naturally, safely and effectively way.

A valid alternative to the classic treatment with bactericidal and/or antifungal compounds is the induction of the endogenous defense systems of organisms and, specifically, the induction of endogenous β-defensin expression. The state of the art describes that hBD2 and hBD3 expression is inducible, and can be stimulated by means of bacteria or yeast extracts [Harder J., Bartels J., Christophers E. and Schröder J. M. (1997) "A peptide antibiotic from human skin" Nature 387: 861], by isoleucine [Fehlbaum P., Rao M., Zasloff M. and Anderson G. M. (2000) "An essential amino acid induces epithelial β-defensin expression" PNAS 97:12723-12728] or by alkylamines [Bukowski J. F., Morita C. T. and Brenner M. B. (1999) "Human gamma delta T cells recognize alkylamines derived from microbes, edible plants, and tea: implications for innate immunity" Immunity 11:57-65].

Different patents and applications describe the use of plant extracts as agents inducing β-defensin expression. Application FR 2,843,125 A1 of Coletica S. A. and YSL Beauté describes the use of certain plant extracts, among them boldo extract, as well as the use of vitamin A and its precursors, α-MSH and its peptide fragments or analogs, calcium and its salts or isoleucine esters as hBD production stimulators, with the compromise that they do not stimulate pro-inflammatory molecule production, and their application in the cosmetic and pharmaceutical field as antifungal or antibacterial agents. International application WO 2005/077349 A1 of Otsuka Pharmaceuticals Co. describes the use of different plant extracts, protein hydrolysates, amino acids, enzymes or proteins as agents inducing hBD synthesis and their use in the cosmetic, food or pharmaceutical field. Patent application JP 2005-270117 A of Morinaga Co. also describes the use of different plant extracts as agents stimulating hBD expression.

Other documents such as patent application US 2004/0259795 A1 of Gemma Biotechnology Ltd. describe the use of proteins such as the CD14 milk protein or fragments thereof as agents stimulating defensin synthesis and their application as a medicinal product or dietary agent for reducing sepsis symptoms.

The state of the art also describes certain types of small molecules which are capable of inducing hBD synthesis. International application WO 01/68085 A1 of Genaera Corp. and patent application US 2002/0076393 A1 of Magainin Pharmaceuticals Inc. describe the use of the amino acids isoleucine or valine, their stereoisomers and some analogs of said amino acids in the treatment or prevention of infectious processes through the induction of hBD expression. Likewise, application EP 1,671,629 A1, also of Otsuka Pharmaceuticals Co., describes the use of certain organic acids, specifically fumaric, malic, citric, ascorbic, lactic, acetic, adipic, tartaric, cinnamic, glutamic or succinic acids as hBD expression inducers. International patent application WO 2005/115403 A2 of the Cedars Sinai Medical Center describes a method for treating a condition comprising the administration of vitamin D3 or its analogs as endogenous hBD production stimulators, and its use in the pharmaceutical or dermopharmaceutical field. Patent application FR 2,896,691 A1 of Pierre Fabre Dermo-Cosmetique S. A. describes the use of alkylglucoside esters as hBD expression inducers and their use in the dermatological or dermocosmetological field.

In the same way, it is known in the state of the art that some microorganisms or microorganism extracts have an efficacy inducing endogenous hBD expression. Patent application US 2005/0196480 A1 of Estee Lauder Companies describes the use of Lactobacillus extracts as hBD production stimulators, and their application in the cosmetic field for the reduction of skin microflora, the treatment of acne and the reduction of sensitivity of sensitive skin. International patent application WO 2004/055041 A2 of Case Western Reserve University describes a defensin-stimulating composition comprising a 12 kDa defensin-inducing peptide associated to fusobacterium and its use for the treatment of infections caused by the human immunodeficiency virus. Application FR 2,879,452 A1 of L'Oreal describes the hBD synthesis-inducing capacity of a non-photosynthetic, non-fructifying filamentous bacterium, and its use in the cosmetic field. Patent U.S. Pat. No. 6,984,622 B2 of The Regents of the University of California describes the use of lipopolysaccharide or its fragments as agents stimulating hBD expression for the treatment or prevention of ocular infections and of ocular wounds. International application WO 2007/020884 A1 of Meiji Dairies Corp. describes the use of bifidobacteria and lactic acid bacteria extracts for the prevention of infections by increasing endogenous 13-defensin levels. Patent application JP 2006-241023 A of Asahi Breweries Ltd. describes the use of mannose-rich yeast as an agent inducing defensin synthesis and its use in the pharmaceutical and food field.

None of the documents known in the state of the art describes peptides not derived from natural products capable of inducing hBD expression.

SUMMARY OF THE INVENTION

The present invention provides a solution to the problem mentioned above. The applicant of the present invention has surprisingly discovered that certain peptide derivatives, whose amino acid sequence is not derived from natural products, are capable of inducing hBD expression, particularly human β defensin-2 and/or β defensin-3 expression.

The peptide derivatives of the present invention therefore provide a simple, effective and risk-free solution for the treatment, care and/or cleansing of the skin, mucosae, scalp and/or nails, comprising the application to the skin, mucosae, scalp and/or nails or the oral or parenteral administration to a mammal of a peptide derivative of general formula (I) as defined below.

In a first aspect, the invention relates to a peptide derivative according to general formula (I)

$$R^1\text{-AA}^1\text{-AA}^2\text{-AA}^3\text{-AA}^4\text{-R}^2 \quad (I)$$

its stereoisomers, mixtures thereof, or its cosmetically or pharmaceutically acceptable salts, characterized in that:
  AA$^1$ is selected from the group consisting of -Glu- and -Arg-;
  AA$^2$ is selected from the group consisting of -Met-, -Ahx- and -Phg-;
  AA$^3$ is selected from the group consisting of -Ala- and -Phg-;
  AA$^4$ is selected from the group consisting of -Ile- or a single bond;
  R$^1$ is selected from the group consisting of H, substituted or non-substituted non-cyclic aliphatic group, substituted or non-substituted alicyclyl, substituted or non-substituted heterocyclyl, substituted or non-substituted heteroarylalkyl, substituted or non-substituted aryl, substituted or non-substituted aralkyl, and R$^5$—C(O)—; and $R^2$ is selected from the group consisting of —$NR^3R^4$, —$OR^3$ and —$SR^3$; wherein $R^3$ and $R^4$ are independently selected from the group consisting of H, substituted or non-substituted non-cyclic aliphatic group, substituted or non-substituted alicyclyl, substituted or non-substituted heterocyclyl, substituted or non-substituted heteroarylalkyl, substituted or non-substituted aryl and substituted or non-substituted aralkyl;

wherein $R^5$ is selected from the group consisting of H, substituted or non-substituted non-cyclic aliphatic group, substituted or non-substituted alicyclyl, substituted or non-substituted aryl, substituted or non-substituted aralkyl, substituted or non-substituted heterocyclyl and substituted or non-substituted heteroarylalkyl.

Another aspect of the present invention is a process for obtaining these peptide derivatives of general formula (I).

Another aspect of the present invention is aimed at a cosmetic or pharmaceutical composition comprising a cosmetically or pharmaceutically effective amount of at least one peptide derivative of general formula (I), its stereoisomers, mixtures thereof or its cosmetically and pharmaceutically acceptable salts and at least one cosmetically or pharmaceutically acceptable excipient or adjuvant.

In another aspect, the invention is aimed at the use of a peptide derivative of general formula (I), its stereoisomers, mixtures thereof or its cosmetically or pharmaceutically acceptable salts, in the preparation of a cosmetic or pharmaceutical composition for the treatment, care and/or cleansing of the skin, mucosae, scalp and/or nails.

DETAILED DESCRIPTION OF THE INVENTION

The peptide derivatives of the invention are synthetic peptide derivatives, not derived from natural products, which, as is shown in the examples, have an important β-defensin-inducing activity and are therefore useful for the treatment, care and prevention of those conditions, disorders and/or pathologies of the skin, mucosae, scalp and/or nails resulting from microorganism proliferation or being at risk of microorganism proliferation.

DEFINITIONS

For the purpose of facilitating the understanding of the present invention, the meanings of some terms and expressions as they are used in the context of the invention are included.

In the present description the abbreviations used for the amino acids follow the rules of the IUPAC-IUB Commission on Biochemical nomenclature specified in *Eur. J. Biochem.* (1984) 138, 9-37 and in *J. Biol. Chem.* (1989) 264, 633-673.

Thus, for example, Gly represents $NH_2$—$CH_2$—C(O)—OH, Gly- represents —$NH_2$—$CH_2$—C(O)—, -Gly represents —NH—$CH_2$—C(O)—OH and -Gly- represents —NH—$CH_2$—C(O)—. The hyphen, representing the peptide bond, therefore eliminates the OH from the 1-carboxyl group of the amino acid (represented herein in the conventional non-ionized form) when it is placed to the right of the symbol, and eliminates the H from the 2-amino group of the amino acid when it is placed to the left of the symbol; both modifications can be applied to the same symbol (see Table 1).

TABLE 1

| Symbol | Residue |
|---|---|
| -Glu- | (structure of glutamic acid residue with —COOH side chain) |
| -Phg- | (structure of phenylglycine residue with phenyl side chain) |
| -Arg- | (structure of arginine residue with guanidino side chain) |
| -Ala- | (structure of alanine residue with methyl side chain) |
| -Met- | (structure of methionine residue with —S—CH₃ side chain) |
| -Ile- | (structure of isoleucine residue) |
| -Ahx- | (structure of 6-aminohexanoic acid residue) |

The abbreviation "Ac-" is used in the present description to designate the acetyl ($CH_3$—C(O)—) group and the abbreviation "Palm-" is used to designate the palmitoyl ($CH_3$—$(CH_2)_{14}$—C(O)—) group.

The term "non-cyclic aliphatic group" is used in the present invention to cover, for example and in a non-limiting sense, linear or branched alkyl, alkenyl and alkynyl groups.

The term "alkyl group" relates to a linear or branched saturated group having between 1 and 24, preferably between 1 and 16, even more preferably between 1 and 14, still more preferably between 1 and 12, still more preferably 1, 2, 3, 4, 5 or 6 carbon atoms and which is bound to the rest of the molecule by means of a single bond, including, for example and in a non-limiting sense, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and the like.

The term "alkenyl group" relates to a group having between 2 and 24, preferably between 2 and 16, even more preferably between 2 and 14, still more preferably between 2 and 12, still more preferably 2, 3, 4, 5 or 6 carbon atoms, with one or more carbon-carbon double bonds, preferably with 1, 2 or 3 carbon-carbon double bonds, conjugated or non-conjugated, which is bound to the rest of the molecule by means of a single bond, including, for example and in a non-limiting sense, the vinyl, oleyl, linoleyl group and the like.

The term "alkynyl group" relates to a group having between 2 and 24, preferably between 2 and 16, even more preferably between 2 and 14, still more preferably between 2 and 12, still more preferably 2, 3, 4, 5 or 6 carbon atoms with one or more carbon-carbon triple bonds, preferably 1, 2 or 3 carbon-carbon triple bonds, conjugated or non-conjugated, which is bound to the rest of the molecule by means of a single bond, including, for example and in a non-limiting sense, the ethynyl, 1-propynyl, 2-propynyl, 1-butynyl, 2-butynyl, 3-butynyl, pentynyl group, such as for example 1-pentynyl, and the like.

The term "alicyclyl group" is used in the present invention to cover, for example and in a non-limiting sense, cycloalkyl or cycloalkenyl or cycloalkynyl groups.

The term "cycloalkyl" relates to a saturated mono- or polycyclic aliphatic group having between 3 and 24, preferably between 3 and 16, even more preferably between 3 and 14, still more preferably between 3 and 12, still more preferably 3, 4, 5 or 6 carbon atoms and which is bound to the rest of the molecule by means of a single bond, including, for example and in a non-limiting sense, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and the like.

The term "cycloalkenyl" relates to a non-aromatic mono- or polycyclic aliphatic group having between 5 and 24, preferably between 5 and 16, even more preferably between 5 and 14, still more preferably between 5 and 12, still more preferably 5 or 6 carbon atoms, with one or more carbon-carbon double bonds, preferably 1, 2 or 3 carbon-carbon double bonds, conjugated or non-conjugated, and which is bound to the rest of the molecule by means of a single bond, including, for example and in a non-limiting sense, the cyclopent-1-en-1-yl group and the like.

The term "cycloalkynyl" relates to a non-aromatic mono- or polycyclic aliphatic group having between 5 and 24, preferably between 5 and 16, even more preferably between 5 and 14, still more preferably between 5 and 12, still more preferably 5 or 6 carbon atoms, with one or more carbon-carbon triple bonds, preferably 1, 2 or 3 carbon-carbon triple bonds, conjugated or non-conjugated, and which is bound to the rest of the molecule by means of a single bond, including, for example and in a non-limiting sense, the cyclohex-1-yn-1-yl group and the like.

The term "aryl group" relates to an aromatic group having between 6 and 30, preferably between 6 and 18, even more preferably between 6 and 10, still more preferably 6 or 10 carbon atoms, comprising 1, 2, 3 or 4 aromatic nuclei, bound by means of a carbon-carbon bond or fused, including, for example and in a non-limiting sense, phenyl, naphthyl, diphenyl, indenyl, phenanthryl or anthranyl among others; or to an aralkyl group.

The term "aralkyl group" relates to an alkyl group substituted with an aromatic group, having between 7 and 24 carbon atoms and including, for example and in a non-limiting sense, —(CH$_2$)$_{1-6}$-phenyl, —(CH$_2$)$_{1-6}$-(1-naphthyl), —(CH$_2$)$_{1-6}$-(2-naphthyl), —(CH$_2$)$_{1-6}$—CH(phenyl)$_2$ and the like.

The term "heterocyclyl group" relates to a 3-10 member hydrocarbon ring, in which one or more of the atoms of the ring, preferably 1, 2 or 3 of the atoms of the ring, is an element different from carbon, such as for example nitrogen, oxygen or sulfur and which can be saturated or unsaturated. For the purposes of this invention, the heterocycle can be a monocyclic, bicyclic or tricyclic cyclic system, which can include systems of fused rings; and the nitrogen, carbon or sulfur atoms can be optionally oxidized in the heterocyclyl radical; the nitrogen atom can be optionally quaternized; and the heterocyclyl radical can be partially or completely saturated or be aromatic. The term heterocyclyl more preferably relates to a 5 or 6 member ring.

The term "heteroarylalkyl group" relates to a an alkyl group substituted with a substituted or non-substituted aromatic heterocyclyl group, the alkyl group having from 1 to 3 carbon atoms and the aromatic heterocyclyl group having between 2 and 24 carbon atoms and from 1 to 3 atoms different from carbon and including, for example and in a non-limiting sense, —(CH$_2$)$_{1-6}$-imidazolyl, —(CH$_2$)$_{1-6}$-triazolyl, —(CH$_2$)$_{1-6}$-thienyl, —(CH$_2$)$_{1-6}$-furyl, —(CH$_2$)$_{1-6}$-pyrrolidinyl and the like.

As understood in this technical area, there can be a certain degree of substitution on the previously defined radicals. Thus, there can be substitution in any of the groups of the present invention. The references of the present document to substituted groups in the groups of the present invention indicate that the specified radical can be substituted in one or more available positions by one or more substituents, preferably in 1, 2 or 3 positions, more preferably in 1 or 2 positions, still more preferably in 1 position. Said substituents include, for example and in a non-limiting sense, C$_1$-C$_4$ alkyl; hydroxyl; C$_1$-C$_4$ alkoxyl; amino; C$_1$-C$_4$ aminoalkyl; C$_1$-C$_4$ carbonyloxyl; C$_1$-C$_4$ oxycarbonyl; halogen such as fluorine, chlorine, bromine and iodine; cyano; nitro; azido; C$_1$-C$_4$ alkylsulfonyl; thiol; C$_1$-C$_4$ alkylthio; aryloxyl such as phenoxyl; —NR$^b$(C=NR$^b$)NR$^b$R$^c$; wherein R$^b$ and R$^c$ are independently selected from the group consisting of H, C$_1$-C$_4$ alkyl, C$_2$-C$_4$ alkenyl, C$_2$-C$_4$ alkynyl, C$_3$-C$_{10}$ cycloalkyl, C$_6$-C$_{18}$ aryl, C$_7$-C$_{17}$ aralkyl, 3-10 member heterocyclyl or protective group of the amino group.

Compounds of the Invention

The compounds of the invention are defined by general formula (I)

$$R^1\text{-AA}^1\text{-AA}^2\text{-AA}^3\text{-AA}^4\text{-R}^2 \qquad (I)$$

wherein R$^1$, AA$^1$, AA$^2$, AA$^3$, AA$^4$ and R$^2$ have the previously defined meaning.

The reference to "single bond" in the case of AA$^4$ means that the amino acid is absent in this case. Therefore, the peptide derivatives of the invention are either tetrapeptide derivatives if AA$^4$ is present or tripeptide derivatives if AA$^4$ is a single bond.

The R$^1$ and R$^2$ groups are bound to amino-terminal and carboxy-terminal ends of the peptide sequences.

According to an embodiment of the present invention, the AA$^1$, AA$^2$, AA$^3$ and AA$^4$ groups are derived from amino acids with L (levogyrate) configuration. According to a preferred embodiment, $R^1$ is selected from the group consisting of H or $R^5$—C(O)—, wherein $R^5$ is selected from the group consisting of substituted or non-substituted $C_1$-$C_{24}$ alkyl radical, substituted or non-substituted $C_2$-$C_{24}$ alkenyl, substituted or non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, substituted or non-substituted $C_7$-$C_{24}$ aralkyl, substituted or non-substituted 3-10 member ring heterocyclyl, and substituted or non-substituted heteroarylalkyl of 2 to 24 carbon atoms and from 1 to 3 atoms different from carbon and an alkyl chain of 1 to 3 carbon atoms. More preferably, $R^1$ is selected from H, acetyl, tert-butanoyl, hexanoyl, 2-methylhexanoyl, cyclohexanecarboxyl, octanoyl, decanoyl, lauroyl, myristoyl, palmitoyl, stearoyl, oleoyl and linoleoyl. Even more preferably, $R^1$ is H, acetyl, lauroyl, myristoyl or palmitoyl. In an even more preferred embodiment, the $R^1$ radicals are acetyl or palmitoyl.

According to another preferred embodiment, $R^2$ is —$NR^3R^4$, —$OR^3$ or —$SR^3$, wherein $R^3$ and $R^4$ are independently selected from the group consisting of H, substituted or non-substituted $C_1$-$C_{24}$ alkyl, substituted or non-substituted $C_2$-$C_{24}$ alkenyl, substituted or non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, substituted or non-substituted $C_7$-$C_{24}$ aralkyl, substituted or non-substituted 3-10 member ring heterocyclyl, and substituted or non-substituted heteroarylalkyl of 2 to 24 carbon atoms and from 1 to 3 atoms different from carbon. Optionally, $R^3$ and $R^4$ can be bound by means of a saturated or unsaturated carbon-carbon bond, forming a cycle with the nitrogen atom. More preferably, $R^2$ is —$NR^3R^4$ or —$OR^3$, wherein $R^3$ and $R^4$ are independently selected from the group consisting of H, substituted or non-substituted $C_1$-$C_{24}$ alkyl, substituted or non-substituted $C_2$-$C_{24}$ alkenyl, substituted or non-substituted $C_2$-$C_{24}$ alkynyl, substituted or non-substituted $C_3$-$C_{10}$ cycloalkyl, substituted or non-substituted $C_6$-$C_{15}$ aryl and substituted or non-substituted 3-10 member heterocyclyl, substituted or non-substituted heteroarylalkyl with a 3 to 10 member ring and an alkyl chain of 1 to 3 carbon atoms.

Even more preferably, $R^2$ is selected from the group consisting of —$NR^3R^4$ and —$OR^3$, wherein $R^3$ and $R^4$ are the same or different. More preferably, $R^3$ and $R^4$ are selected from the group consisting of H, methyl, ethyl, hexyl, dodecyl or hexadecyl. More preferably, $R^3$ is H and $R^4$ is selected from the group consisting of H, methyl, ethyl, hexyl, dodecyl or hexadecyl.

According to an even more preferred embodiment, $R^2$ is selected from —OH and —$NH_2$.

Even more preferably, $R^1$ is acetyl and $R^2$ is —OH.

According to an embodiment of the present invention, $AA^1$ is -Glu-, $AA^2$ is -Met-, $AA^3$ is -Ala- and $AA^4$ is -Ile-.

According to another embodiment of the present invention, $AA^1$ is -Arg-, $AA^2$ is -Ahx-, $AA^3$ is -Ala- and $AA^4$ is a single bond.

According to another embodiment of the present invention, $AA^1$ is -Arg-, $AA^2$ is -Phg-; $AA^3$ is -Phg- and $AA^4$ is a single bond.

According to another embodiment of the present invention, $R^1$ is selected from the group consisting of H, acetyl, lauroyl, myristoyl or palmitoyl, $AA^1$ is -L-Glu-, $AA^2$ is -L-Met-, $AA^3$ is -L-Ala-, $AA^4$ is -L-Ile- and $R^2$ is —$NR^3R^4$ or —$OR^3$, wherein $R^3$ and $R^4$ are independently selected from H, methyl, ethyl, hexyl, dodecyl and hexadecyl groups, preferably $R^2$ is —OH or —$NH_2$. Even more preferably, $R^1$ is acetyl and $R^2$ is —OH.

According to another embodiment of the present invention, $R^1$ is selected from the group consisting of H, acetyl, lauroyl, myristoyl or palmitoyl, $AA^1$ is -L-Arg-, $AA^2$ is -Ahx-, $AA^3$ is -L-Ala-, $AA^4$ is a single bond and $R^2$ is —$NR^3R^4$ or —$OR^3$, wherein $R^3$ and $R^4$ are independently selected from H, methyl, ethyl, hexyl, dodecyl and hexadecyl groups, preferably $R^2$ is —OH or —$NH_2$. Even more preferably, $R^1$ is acetyl and $R^2$ is —OH.

According to another embodiment of the present invention, $R^1$ is selected from the group consisting of H, acetyl, lauroyl, myristoyl or palmitoyl, $AA^1$ is -L-Arg-, $AA^2$ is -L-Phg- or -D-Phg-, $AA^3$ is -L-Phg- or -D-Phg-, $AA^4$ is a single bond and $R^2$ is —$NR^3R^4$ or —$OR^3$, wherein $R^3$ and $R^4$ are independently selected from H, methyl, ethyl, hexyl, dodecyl and hexadecyl groups, preferably $R^2$ is —OH or —$NH_2$. Even more preferably, $R^1$ is acetyl and $R^2$ is —OH.

The compounds of formula (I) are preferably selected from the group consisting of:
Ac-Arg-Phg-Phg-OH,
Ac-Glu-Phg-Ala-OH,
Ac-Arg-Phg-Ala-Ile-OH (Ac-SEQ ID No. 1-OH),
Ac-Arg-Ahx-Phg-Ile-OH (Ac-SEQ ID No. 2-OH), H-Glu-Met-Ala-Ile-OH(H-SEQ ID No. 3-OH), Ac-Arg-Met-Phg-Ile-OH (Ac-SEQ ID No. 4-OH),
Ac-Arg-Phg-Ala-OH,
Ac-Glu-Phg-Ala-Ile-OH (Ac-SEQ ID No. 5-OH),
Ac-Glu-Met-Phg-Ile-OH (Ac-SEQ ID No. 6-OH),
Ac-Arg-Ahx-Ala-OH,
Ac-Arg-Phg-Phg-NH—$(CH_2)_{15}$—$CH_3$,
Palm-Glu-Met-Ala-Ile-$NH_2$ (Palm-SEQ ID No. 3-$NH_2$),
Ac-Arg-Ahx-Ala-Ile-OH (Ac-SEQ ID No. 7-OH),
Ac-Arg-Phg-Phg-Ile-OH (Ac-SEQ ID No. 8-OH),
Ac-Glu-Phg-Phg-Ile-OH (Ac-SEQ ID No. 9-OH),
Ac-Arg-Met-Ala-Ile-OH (Ac-SEQ ID No. 10-OH),
and
Ac-Glu-Met-Ala-Ile-OH (Ac-SEQ ID No. 3-OH).

The peptide derivatives of the present invention can exist as stereoisomers or mixtures of stereoisomers; for example, the amino acids forming them can have L-, D-configuration, or be racemic independently from one another. It is therefore possible to obtain isomeric mixtures as well as racemic mixtures or diastereomeric mixtures, or pure diastereoisomers or enantiomers, depending on the number of asymmetric carbons and on which isomers or isomeric mixtures are present. The preferred structures of the peptide derivatives of the invention are pure isomers, i.e., enantiomers or diastereoisomers.

For example, when it is indicated that $AA^1$ can be -Glu-, it is understood that $AA_1$ is selected from -L-Glu-, -D-Glu- or racemic or non-racemic mixtures of both. Likewise, when it is stated that $AA^2$ can be -Met-, it is understood that it can be -L-Met-, -D-Met- or racemic or non-racemic mixtures of both. The methods described herein allow the person skilled in the art to obtain each of the stereoisomers of the peptide derivative of the invention by means of choosing the amino acid with the suitable configuration.

Thus, the compounds of formula (I) are even more preferably selected from the group consisting of:
Ac-L-Arg-L-Phg-L-Phg-OH,
Ac-L-Arg-L-Phg-D-Phg-OH,
Ac-L-Arg-D-Phg-L-Phg-OH,
Ac-L-Arg-D-Phg-D-Phg-OH,
Ac-L-Glu-L-Phg-L-Ala-OH,
Ac-L-Glu-D-Phg-L-Ala-OH, Ac-L-Arg-L-Phg-L-Ala-L-Ile-OH (Ac-SEQ ID No. 11-OH),
Ac-L-Arg-D-Phg-L-Ala-L-Ile-OH (Ac-SEQ ID No. 12-OH),
Ac-L-Arg-Ahx-L-Phg-L-Ile-OH (Ac-SEQ ID No. 13-OH),
Ac-L-Arg-Ahx-D-Phg-L-Ile-OH (Ac-SEQ ID No. 14-OH),
H-L-Glu-L-Met-L-Ala-L-Ile-OH(H-SEQ ID No. 3-OH),
Ac-L-Arg-L-Met-L-Phg-L-Ile-OH (Ac-SEQ ID No. 15-OH),
Ac-L-Arg-L-Met-D-Phg-L-Ile-OH (Ac-SEQ ID No. 16-OH),
Ac-L-Arg-L-Phg-L-Ala-OH,
Ac-L-Arg-D-Phg-L-Ala-OH,
Ac-L-Glu-L-Phg-L-Ala-L-Ile-OH (Ac-SEQ ID No. 17-OH),
Ac-L-Glu-D-Phg-L-Ala-L-Ile-OH (Ac-SEQ ID No. 18-OH),
Ac-L-Glu-L-Met-L-Phg-L-Ile-OH (Ac-SEQ ID No. 19-OH),
Ac-L-Glu-L-Met-D-Phg-L-Ile-OH (Ac-SEQ ID No. 20-OH),
Ac-L-Arg-Ahx-L-Ala-OH,
Ac-L-Arg-L-Phg-L-Phg-NH—$(CH_2)_{15}$—$CH_3$,
Ac-L-Arg-L-Phg-D-Phg-NH—$(CH_2)_{15}$—$CH_3$,
Ac-L-Arg-D-Phg-L-Phg-NH—$(CH_2)_{15}$—$CH_3$,
Ac-L-Arg-D-Phg-D-Phg-NH—$(CH_2)_{15}$—$CH_2$,
Palm-L-Glu-L-Met-L-Ala-L-Ile-$NH_2$ (Palm-SEQ ID No. 3-$NH_2$),
Ac-L-Arg-Ahx-L-Ala-L-Ile-OH (Ac-SEQ ID No. 7-OH),
Ac-L-Arg-L-Phg-L-Phg-L-Ile-OH (Ac-SEQ ID No. 21-OH),
Ac-L-Arg-L-Phg-D-Phg-L-Ile-OH (Ac-SEQ ID No. 22-OH),
Ac-L-Arg-D-Phg-L-Phg-L-Ile-OH (Ac-SEQ ID No. 23-OH),
Ac-L-Arg-D-Phg-D-Phg-L-Ile-OH (Ac-SEQ ID No. 24-OH),
Ac-L-Glu-L-Phg-L-Phg-L-Ile-OH (Ac-SEQ ID No. 25-OH),
Ac-L-Glu-L-Phg-D-Phg-L-Ile-OH (Ac-SEQ ID No. 26-OH),
Ac-L-Glu-D-Phg-L-Phg-L-Ile-OH (Ac-SEQ ID No. 27-OH),
Ac-L-Glu-D-Phg-D-Phg-L-Ile-OH (Ac-SEQ ID No. 28-OH),
Ac-L-Arg-L-Met-L-Ala-L-Ile-OH (Ac-SEQ ID No. 10-OH),
Ac-L-Glu-L-Met-L-Ala-L-Ile-OH (Ac-SEQ ID No. 3-OH), and
their mixtures or their cosmetically or pharmaceutically acceptable salts.

The cosmetically or pharmaceutically acceptable salts of the peptide derivatives provided by this invention are also within the scope of the present invention. The term "cosmetically or pharmaceutically acceptable salts" means a salt generally admitted for its use in animals and more particularly in human beings, and includes the salts used to form base addition salts, either inorganic base addition salts, such as for example and in a non-limiting sense, lithium, sodium, potassium, calcium, magnesium or aluminium among others, or organic base addition salts, such as for example and in a non-limiting sense ethylamine, diethylamine, ethylenediamine, ethanolamine, diethanolamine, arginine, lysine, histidine or piperazine among others, or acid addition salts, either organic acid addition salts, such as for example and in a non-limiting sense acetate, citrate, lactate, malonate, maleate, tartrate, fumarate, benzoate, aspartate, glutamate, succinate, oleate, trifluoroacetate, oxalate, pamoate or gluconate among others, or inorganic acid addition salts, such as for example and in a non-limiting sense chloride, sulfate, borate or carbonate among others. The nature of the salt is not critical, provided that it is cosmetically or pharmaceutically acceptable. The cosmetically or pharmaceutically acceptable salts of the peptide derivatives of the invention can be obtained by conventional methods well known in the state of the art [Berge S. M., Bighley L. D. and Monkhouse D. C. (1977) "*Pharmaceutical Salts*" *J. Pharm. Sci.* 66:1-19].

Methods of Preparation

The synthesis of the peptide derivatives of the invention, their stereoisomers or their cosmetically or pharmaceutically acceptable salts can be carried out according to conventional methods known in the state of the art, such as for example by means solid-phase peptide synthesis methods [Stewart J. M. and Young J. D. (1984) "*Solid Phase Peptide Synthesis, 2nd edition*" Pierce Chemical Company, Rockford, Ill.; Bodanzsky M. and Bodanzsky A. (1984) "*The practice of Peptide Synthesis*" Springer Verlag, New Cork; Lloyd-Williams P., Albericio F. and Giralt E. (1997) "*Chemical Approaches to the Synthesis of Peptides and Proteins*" CRC, Boca Raton, Fla., USA], solution synthesis, a combination of solid-phase synthesis and solution synthesis methods or enzymatic synthesis methods [Kullmann W. (1980) "*Proteases as catalysts for enzymic syntheses of opioid peptides*" *J. Biol. Chem.* 255:8234-8238]. The peptide derivatives can also be obtained by fermentation of a bacterial strain that is modified or unmodified by genetic engineering for the purpose of producing the desired sequences, or by controlled hydrolysis of proteins of animal or plant origin, preferably plant origin, which releases peptide fragments containing at least the desired sequence.

For example, a method for obtaining the peptide derivatives of the invention of formula (I) comprises the steps of:
a. Coupling an amino acid with the N-terminal end protected and the C-terminal end free to an amino acid with the N-terminal end free and the C-terminal end protected or bound to a solid support;
b. Eliminating the protecting group of the N-terminal end;
c. Repeating the sequence of coupling and eliminating the protecting group of the N-terminal end a.-b. until obtaining the desired sequence -$AA^1$-$AA^2$-$AA^3$-$AA^4$-sequence;
d. Eliminating the protecting group of the C-terminal end or cleaving from the solid support.

The C-terminal end is preferably bound to a solid support and the process is carried out on solid phase and therefore comprises coupling an amino acid with the N-terminal end protected and the C-terminal end free on an amino acid with the N-terminal end free and the C-terminal end bound to a polymeric support; eliminating the protecting group of the N-terminal end; and repeating this sequence as many times as necessary to thus obtain a tripeptide or a tetrapeptide, finally followed by cleaving the synthesized peptide from the original polymeric support.

The functional groups of the side chains of the amino acids, if any, are kept suitably protected with temporary or permanent protecting groups throughout the synthesis, and can be deprotected simultaneously or orthogonally to the process of cleaving the peptide from the polymeric support.

Solid-phase synthesis can alternatively be carried out by means of a convergent strategy coupling a dipeptide or a tripeptide to the polymeric support or to a dipeptide or amino acid previously bound to the polymeric support. Convergent synthesis strategies are extensively known by persons skilled in the art and are described in Lloyd-Williams P., Albericio F. and Giralt E. in "*Convergent solid-phase peptide synthesis*" (1993) *Tetrahedron* 49:11065-11133.

An example of a process for obtaining the peptide derivatives of the invention of formula (I)

$$R^1\text{-}AA^1\text{-}AA^2\text{-}AA^3\text{-}AA^4\text{-}R^2 \qquad (I)$$

comprises the steps of
sequentially reacting a fragment of formula (II)

$$PG^1\text{-}AA^n\text{-}OH \qquad (II)$$

having the C-terminal carboxyl group free or a reactive derivative thereof, wherein $PG_1$ is a protecting group of the N-terminal group and $AA^n$ is an amino acid moiety ($\text{-}AA^1\text{-}$, $\text{-}AA^2\text{-}$ or $\text{-}AA^3\text{-}$) as has been previously described, with a complementary fragment
(III) having an amino group at the N-terminal end with at least one free hydrogen atom, $$H\text{-}AA^m\text{-}Sop \qquad (III)$$

wherein Sop is a protecting group or a solid support and $AA^m$ is an amino acid moiety $\text{-}AA^3\text{-}$ or $\text{-}AA^4\text{-}$ as has been previously described, with the consequent formation of an amide type bond and the expansion of the peptide chain in an amino acid moiety to form the fragment of formula (IV), $$PG^1\text{-}AA^n\text{-}AA^m\text{-}Sop \qquad (IV)$$

washing the fragment thus obtained,
cleaving the protecting group $PG^1$ of the fragment thus formed to obtain a fragment (V) with the N-terminal end free and $$H\text{-}AA^n\text{-}AA^m\text{-}Sop \qquad (V)$$

repeating the sequence of coupling, washing and cleaving the protecting group as many times as necessary until obtaining a precursor of formula (VI)

$$PG\text{-}AA^1\text{-}AA^2\text{-}AA^3\text{-}AA^4\text{-}Sop \qquad (VI)$$

wherein PG is a protecting group, and Sop and $AA^1$-$AA^2$-$AA^3$-$AA^4$ have the previously described meaning.

The process can comprise the additional steps of deprotecting and/or cleaving from the support the fragment (VI) for the N-terminal and C-terminal ends in indifferent order, using standard processes and conditions known in the art, after which the functional groups of said ends can be modified. The optional modification of the amino- and carboxy-terminal ends can be carried out with the peptide of formula (I) anchored to the polymeric support or once the peptide has been cleaved from the polymeric support. For example, the N-terminal end can first be deprotected to give a fragment of formula (VII).

$$H\text{-}AA^1\text{-}AA^2\text{-}AA^3\text{-}AA^4\text{-}Sop \qquad (VII)$$

Optionally, other types of $R_1$ radical can be introduced by means of the reaction of (VII) with a compound $R^1$—X, wherein $R^1$ has the previously described meaning and X is a leaving group, such as for example and in a non-limiting sense, the tosyl group, the mesyl group and halogen groups among others, by means of a nucleophilic substitution reaction in the presence of a suitable base and solvent and wherein the functional groups of said fragments which do not participate in the formation of the N—C bond, if any, are suitably protected with temporary or permanent protecting groups.

The resulting fragment can be deprotected or cleaved from the solid support, as appropriate, to provide a compound of formula (VIII), which is a peptide of formula (I) wherein $R^2$ is —OH, —NH$_2$ or —SH. Optionally and/or additionally, other $R^2$ radicals can be introduced by means of the reaction of a compound HR$^2$ wherein $R^2$ is –OR$^3$, —NR$^3$R$^4$ or —SR$^3$, with a complementary fragment (IX) corresponding to the compound of formula (VIII) wherein $R^2$ is —OH $$R^1\text{-}AA^1\text{-}AA^2\text{-}AA^3\text{-}AA^4\text{-}OH \qquad (IX)$$

in the presence of a suitable solvent and a base such as for example, N,N-diisopropylethylamine or triethylamine or an additive such as for example, 1-hydroxybenzotriazole (HOBt) or 1-hydroxyazabenzotriazole (HOAt) and a dehydrating agent, such as for example a carbodiimide, a uranium salt, a phosphonium salt or an amidinium salt, among others, or by means of the prior formation of an acyl halide with, for example, thionyl chloride, to thus obtain a peptide derivative according to the invention of general formula (I), wherein the functional groups of said fragments which do not participate in the formation of the N—C bond, if any, are suitably protected with temporary or permanent protecting groups, or alternatively other $R^2$ radicals can be introduced by means of the incorporation simultaneous to the process for cleaving the peptide derivative from the polymeric support.

A person skilled in the art will easily understand that the steps of deprotecting/cleaving the C- and N-terminal ends and their subsequent derivatization can be carried out in indifferent order, according to processes known in the art [Smith, M. B. and March, J. (1999) "*March's Advanced Organic Chemistry Reactions, Mechanisms and Structure*", 5th Edition, John Wiley & Sons, 2001].

The term "protecting group" relates to a group blocking an organic functional group and which can be eliminated in controlled conditions. The protecting groups, their relative reactivities and the conditions in which they remain inert are known by persons skilled in the art.

Examples of representative protecting groups for the amino group are amides, such as acetate amide, benzoate amide, pivalate amide; carbamates, such as benzyloxycarbonyl (Cbz), p-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), allyloxycarbonyl (Alloc), 9-fluorenylmethyloxycarbonyl (Fmoc), among others; preferably, Boc or Fmoc.

Examples of representative groups for the carboxyl group are esters, such as tert-butyl (tBu) ester, allyl (All) ester, triphenylmethyl ester (trityl (Trt) ester), cyclohexyl (cHex) ester, benzyl (Bzl) ester, o-nitrobenzyl ester, p-nitrobenzyl ester, p-methoxybenzyl ester, trimethylsilylethyl ester, among others; preferred protecting groups of the invention are allyl, tert-butyl, cyclohexyl, benzyl and trityl esters.

Trifunctional amino acids, if any, are protected during the synthetic process with temporary or permanent protecting groups orthogonal to the protecting groups of the amino- and carboxy-terminal ends. The guanidine group of arginine can be protected with the 2,2,5,7,8-pentamethylchroman-6-sulfonyl (Pmc), 2,2,4,6,7-pentamethyl-dihydrobenzofuran-5-sulfonyl (Pbf), para-toluenesulfonyl (tosyl, Tos) or 4-methoxy-2,3,6-trimethylbenzenesulfonyl (Mtr) group, among others, and the carboxyl group of glutamic acid can be protected with the tert-butyl (tBu) group, the trityl (Trt) group, the cyclohexyl (cHex) group, the benzyl (Bzl) group or the allyl (All) group, among others.

In a preferred embodiment, the protecting group strategy used is the strategy in which the amino groups are protected by means of Boc, the carboxyl groups are protected by means of Bzl, cHex or All, and the arginine side chain is protected with Mtr or Tos and the glutamic side chain with Bzl, cHex or All.

In another preferred embodiment, the protecting group strategy used is the strategy in which the amino groups are protected by means of Fmoc, the carboxyl groups are protected by means of tBu, All or Trt, and the arginine side chain is protected with Pmc or Pbf and the glutamic side chain with tBu, All or Trt.

Examples of these and additional protecting groups, their introduction and their elimination are described in the literature [Greene T. W. and Wuts P. G. M., (1999) *"Protective groups in organic synthesis"* John Wiley & Sons, New York; Atherton B. and Sheppard R. C. (1989) *"Solid Phase Peptide Synthesis: A practical approach"* IRL Oxford University Press]. The term "protecting groups" also includes polymeric supports used in solid-phase synthesis.

When the synthesis is carried out completely or partially on solid phase, the following can be mentioned as solid supports to be used in the method of the invention: supports made of polystyrene, polyethylene glycol-grafted polystyrene and the like, such as for example and in a non-limiting sense p-methylbenzhydrylamine (MBHA) resins [Matsueda G. R. and Stewart J. M. (1981) *"A p-methylbenzhydrylamine resin for improved solid-phase synthesis of peptide amides"* Peptides 2:45-50], 2-chlorotrityl resins [Barlos K., Gatos D., Kallitsis J., Papaphotiu G., Sotiriu P., Wenqing Y. and Schafer W. (1989) *"Darstellung geschützter Peptid-fragmente unter Einsatz substituierter Triphenylmethyl-harze"* Tetrahedron Lett. 30:3943-3946; Barlos K., Gatos D., Kapolos S., Papaphotiu G., Schäfer W. and Wenqing Y. (1989) *"Veresterung von partiell geschützten Peptid-fragmenten mit Harzen. Einsatz von 2-Chlorotritylchlorid zur Synthese von Leu15-gastrin I"* Tetrahedron Lett. 30:3947-3951], TentaGer® resins (Rapp Polymere GmbH), ChemMatrix® resins (Matrix Innovation, Inc) and the like, which may or may not include a labile linker such as 5-(4-aminomethyl-3,5-dimethoxyphenoxy)valeric acid (PAL) [Albericio F., Kneib-Cordonier N., Biancalana S., Gera L., Masada R. I., Hudson D. and Barany G. (1990) *"Preparation and application of 5-(4-(9-fluorenylmethyloxycarbonyl)aminomethyl-3,5-dimethoxy-phenoxy)-valeric acid (PAL) handle for the solid-phase synthesis of C-terminal peptide amides under mild conditions"* J. Org. Chem. 55:3730-3743], 2-[4-aminomethyl-(2,4-dimethoxyphenyl)] phenoxyacetic acid (AM) [Rink H. (1987) *"Solid-phase synthesis of protected peptide fragments using to trialkoxy-diphenyl-methylester resin"* Tetrahedron Lett. 28:3787-3790], Wang [Wang S. S. (1973) *"p-Alkoxybenzyl Alcohol Resin and p-Alkoxybenzyloxycarbonylhydrazide Resin for Solid Phase Synthesis of Protected Peptide Fragments"* J. Am. Chem. Soc. 95:1328-1333] and the like, allowing the deprotection and simultaneous cleavage of the peptide from the polymeric support.

Cosmetic or Pharmaceutical Compositions

The peptide derivatives of the invention can be administered to stimulate hBD synthesis by any means causing the contact of the peptide derivatives with the site of action thereof in the body of a mammal, preferably the body of human beings, and in the form of a composition containing them.

In this sense, another aspect of the invention is a cosmetic or pharmaceutical composition comprising at least one peptide derivative of general formula (I), its stereoisomers, mixtures thereof or its cosmetically or pharmaceutically acceptable salts together with at least one cosmetically or pharmaceutically acceptable adjuvant. Said compositions can be prepared by means of conventional methods known by persons skilled in the art [*"Harry's Cosmeticology"*, Eighth edition (2000) Rieger M. M., ed., New York Chemical Pub., NY, US; *"Remington: The Science and Practice of Pharmacy"*, Twentieth edition (2003) Genaro A. R., ed., Lippincott Williams & Wilkins, Philadelphia, US].

The peptide derivatives of the present invention have a variable water-solubility, according to the nature of their sequence or the possible modifications at the amino- and/or carboxy-terminal ends that they have. The peptide derivatives of the present invention can therefore be incorporated to the compositions by means of aqueous solution, and those which are not water-soluble can be solubilized in conventional cosmetically or pharmaceutically acceptable solvents such as for example and in a non-limiting sense ethanol, propanol, isopropanol, propylene glycol, glycerin, butylene glycol or polyethylene glycol or any combination thereof.

The cosmetically or pharmaceutically effective amount of the peptide derivatives of the invention which must be administered to treat a condition, disorder and/or pathology, as well as their dosage will depend on a number of factors, including the age, condition of the patient, the severity of the disorder or pathology, the administration route and frequency and on the particular nature of the peptide derivatives to be used.

A "cosmetically or pharmaceutically effective amount" is understood as a non-toxic but sufficient amount of peptide derivative or derivatives to provide the desired effect. The peptide derivatives of the invention are used in the cosmetic or pharmaceutical composition of the present invention at cosmetically or pharmaceutically effective concentrations to achieve the desired effect; preferably, with respect to the total weight of the composition, between 0.00000001% (by weight) and 20% (by weight); preferably between 0.000001% (by weight) and 20% (by weight), more preferably between 0.0001% (by weight) and 10% (by weight) and more specifically between 0.0001% (by weight) and 5% (by weight).

The peptide derivatives of the invention can also be incorporated in cosmetic or pharmaceutical sustained release systems and/or delivery systems.

The term "delivery systems" relates to a diluent, adjuvant, excipient or carrier with which the peptide derivative of the invention is administered. Such cosmetic or pharmaceutical carriers can be liquids, such as water, oils or surfactants, including those of petroleum, animal, plant or synthetic origin, such as for example and in a non-limiting sense peanut oil, soybean oil, mineral oil, sesame oil, castor oils, polysorbates, sorbitan esters, ether sulfates, sulfates, betaines, glucosides, maltosides, fatty alcohols, nonoxinols, poloxamers, polyoxyethylenes, polyethylene glycols, dextrose, glycerol and the like. *"Remington's Pharmaceutical Sciences"* by E. W. Martin describes diluents, adjuvants or excipients as suitable carriers.

The term "sustained release" is used in the conventional sense, relating to a delivery system for a compound providing the gradual release of said compound for a time period and preferably, although not necessarily, with constant compound release levels throughout a time period.

Examples of sustained release or delivery systems are liposomes, milliparticles, microparticles, nanoparticles and solid lipid nanoparticles, sponges, vesicles, micelles, millispheres, microspheres and nanospheres, lipospheres, millicapsules, microcapsules and nanocapsules, as well as microemulsions and nanoemulsions, which can be added for the purpose of achieving a greater penetration of the active ingredient and/or improving the pharmacokinetic and pharmacodynamic properties thereof.

The sustained release formulations can be prepared by means of methods known in the state of the art, and the compositions containing them can be administered, for example, by topical administration, including adhesive patches and non-adhesive patches, or by systemic administration, such as for example and in a non-limiting sense by oral, nasal, rectal route, implantation or subcutaneous injection, or implantation or direct injection into a specific part of the body, and they must preferably release a relatively constant amount of the peptide derivatives of the invention. The amount of peptide derivative contained in the sustained release formulation will depend, for example, on the site of administration, the kinetics and duration of the release of the peptide derivative of the invention, as well as the nature of the condition, disorder and/or pathology to be treated or prevented.

The peptide derivatives of the present invention can also be adsorbed on solid organic polymers or solid mineral supports such as for example and in a non-limiting sense talc, bentonite, silica, starch or maltodextrin among others.

The peptide derivatives of the invention can also be incorporated to fabrics, nonwoven fabrics and medical devices which are in direct contact with the skin, mucosae, scalp and/or nails of the body, such that they release the peptide derivatives of the invention either by the biodegradation of the system for anchoring to the fabric, nonwoven fabric or medical devices or by the friction of the latter with the body, by body moisture, by the pH of skin or by body temperature. Likewise, fabrics and nonwoven fabrics can be used to make garments which are in direct contact with the body. Preferably, the fabrics, nonwoven fabrics and medical devices containing the peptide derivatives of the invention are used for the treatment, care and/or cleansing of those conditions, disorders and/or pathologies of the skin resulting from microorganism proliferation, or being at risk of microorganism proliferation, or in the treatment of open wounds.

Examples of fabrics, nonwoven fabrics, garments, medical devices and means for immobilizing the peptide derivatives to them, including the delivery systems and/or the sustained release systems described above, are described in the literature and are known in the state of the art [Schaab C. K. (1986) "*Impregnating Fabrics With Microcapsules*", HAPPI May 1986; Nelson G. (2002) "*Application of microencapsulation in textiles*" Int. J. Pharm. 242:55-62; "*Biofunctional Textiles and the Skin*" (2006) Curr. Probl. Dermatol. v. 33, Hipler U. C. and Elsner P., eds. S. Karger A G, Basel, Switzerland; Malcom R. K., McCullagh S. D., Woolfson A. D., Gorman S. P., Jones D. S, and Cuddy J. (2004) "*Controlled release of a model antibacterial drug from a novel self-lubricating silicone biomaterial*" J. Cont. Release 97:313-320]. Preferred fabrics, nonwoven fabrics, garments and medical devices are bandages, gauzes, T-shirts, socks, pantyhose, underwear, girdles, gloves, diapers, sanitary napkins, dressings, bedspreads, wipes, hydrogels, adhesive patches, non-adhesive patches and/or face masks.

The cosmetic or pharmaceutical preparations containing the peptide derivatives of the present invention, their stereoisomers, mixtures thereof or their cosmetically or pharmaceutically acceptable salts can be used in different types of formulations of topical or transdermal application which will optionally include the cosmetically or pharmaceutically acceptable excipients necessary for the formulation of the desired dosage form [Faulí i Trillo C. (1993) in "*Tratado de Farmacia Galénica*", Luzán 5, S. A. Editions, Madrid].

Topical or transdermal application formulations can be presented in any solid, liquid or semi-solid dosage form, such as for example and in a non-limiting sense, creams, multiple emulsions such as for example and in a non-limiting sense emulsions of oil and/or silicone in water, emulsions of water in oil and/or silicone, emulsions of the water/oil/water or water/silicone/water type and emulsions of the oil/water/oil or silicone/water/silicone type, anhydrous compositions, aqueous dispersions, oils, milks, balsams, foams, lotions, gels, hydroalcoholic solutions, liniments, sera, soaps, shampoos, unguents, mousses, ointments, powders, bars, pencils and sprays or aerosols, including leave-on and rinse-off formulations. These topical or transdermal application formulations can be incorporated by means of the techniques known by people skilled in the art to different types of solid accessories such as for example and in a non-limiting sense wipes, hydrogels, adhesive patches, non-adhesive patches or face masks, or they can be incorporated to different makeup line products such as makeup foundation, makeup removal lotions, makeup removal milks, concealers, eye shadows, lipsticks, lip protectors, lip glosses and powders, among others. The cosmetic or pharmaceutical compositions containing the peptide derivatives of the present invention can also be incorporated to products for the treatment, care and/or cleansing of the nails and cuticles such as nail polishes, nail polish removal lotions and cuticle removal lotions, among others.

The cosmetic or pharmaceutical compositions of the invention can include agents increasing the percutaneous absorption of the peptide derivatives of the present invention, such as for example and in a non-limiting sense dimethylsulfoxide, dimethylacetamide, dimethylformamide, surfactants, azone (1-dodecylazacycloheptan-2-one), alcohol, acetone, propylene glycol or polyethylene glycol among others. The cosmetic or pharmaceutical compositions object of the present invention can likewise be applied to local areas to be treated by means of iontophoresis, sonophoresis, electroporation, occlusive treatment, microinjections or needle-free injections by means of pressure, such as for example injections by oxygen pressure, or any combination thereof, for the purpose of achieving greater penetration of the peptide derivative of the invention. The application area will be determined by the nature of the condition, disorder and/or pathology to be prevented or treated.

The cosmetic compositions containing the peptide derivatives of the present invention, their stereoisomers or their cosmetically or pharmaceutically acceptable salts can likewise be used in different types of formulations for their oral administration, preferably in the form of oral cosmetics, such as for example and in a non-limiting sense, capsules, including gelatin capsules, tablets, including sugar-coated tablets, powders, granulated forms, chewing-gums, solutions, suspensions, emulsions, syrups, jellies or gelatins, as well as in any other presentation known by a person skilled in the art. In particular, the peptide derivatives of the invention can be incorporated in any form of functional food or fortified food, such as for example and in a non-limiting sense, in nutrition bars or in compact or non-compact powders. Said powders can be solubilized in water, soda, dairy products, soy derivatives, or can be incorporated in nutrition bars. The peptide derivatives of the present invention can be formulated with the excipients and adjuvants that are usual for oral compositions or food supplements, such as for example and in a non-limiting sense, fatty components, aqueous components, humectants, preservatives, texturizing agents, flavors, aromas, antioxidants and colorants common in the food industry.

The cosmetic or pharmaceutical compositions containing the peptide derivatives of the invention, their stereoisomers, mixtures thereof or their cosmetically or pharmaceutically acceptable salts can be administered by topical or transdermal route in addition to any other type of suitable route, for example by oral or parenteral route, to which end they will include the pharmaceutically acceptable excipients necessary for the formulation of the desired dosage form. In the context of the present invention, the term "parenteral" includes nasal route, rectal route, subcutaneous injections, intradermal injections, intravascular injections, such as for example intravenous, intramuscular, intravitreal, spinal, intracranial, intraarticular, intrathecal and intraperitoneal injections, as well as any other similar injection or infusion technique. A review of the different pharmaceutical dosage forms of active ingredients and of the excipients necessary for obtaining same can be found, for example, in the "*Tratado de Farmacia Galénica*", C. Faulí i Trillo, 1993, Luzán 5, S. A. Editions, Madrid.

Included among the cosmetically or pharmaceutically acceptable adjuvants contained in the cosmetic or pharmaceutical compositions described in the present invention are the additional ingredients commonly used in compositions for the treatment, care and/or cleansing of the skin, mucosae, scalp and/or nails, such as for example and in a non-limiting sense, agents stimulating or inhibiting melanin synthesis, whitening or depigmenting agents, propigmentation agents, self-tanning agents, anti-aging agents, NO-synthase inhibiting agents, antioxidant agents, free radical-scavengers and/or anti-atmospheric pollution agents, anti-glycation agents, emulsifying agents, emollients, organic solvents, liquid propellants, skin conditioners such as for example humectants, substances that retain moisture, alpha hydroxy acids, beta hydroxy acids, moisturizers, vitamins, pigments or colorants, dyes, gelling polymers, thickeners, surfactants, softeners, anti-wrinkle agents, agents capable of reducing or treating under-eye bags, exfoliating agents, antimicrobial agents, fungicidal agents, fungistatic agents, bactericidal agents, bacteriostatic agents, agents stimulating the synthesis of dermal or epidermal macromolecules and/or capable of inhibiting or preventing their degradation, such as for example agents stimulating collagen synthesis, agents stimulating elastin synthesis, agents stimulating decorin synthesis, agents stimulating laminin synthesis, other agents stimulating defensin synthesis, agents stimulating chaperone synthesis, agents stimulating hyaluronic acid synthesis, agents stimulating the synthesis of lipids and components of the stratum corneum (ceramides, fatty acids, etc.), agents inhibiting collagen degradation, agents inhibiting elastin degradation, agents stimulating fibroblast proliferation, agents stimulating keratinocyte proliferation, agents stimulating keratinocyte differentiation, agents stimulating angiogenesis, skin-relaxing agents, agents stimulating glycosaminoglycan synthesis, DNA repairing agents, DNA protecting agents, anti-itching agents, agents for the treatment of sensitive skin, firming agents, anti-stretch mark agents, astringent agents, agents regulating sebum production, agents stimulating lipolysis, anti-cellulite agents, agents stimulating healing, coadjuvant healing agents, cytokine growth factors, calming agents, anti-inflammatory agents, agents acting on capillary circulation and/or microcirculation, agents acting on cell metabolism, agents intended to improve the dermal-epidermal junction, preservatives, perfumes, chelating agents, plant extracts, essential oils, marine extracts, agents coming from a biofermentation process, mineral salts, cell extracts and sunscreens (organic or mineral photoprotection agents that are active against ultraviolet A and/or B rays) among others, provided that they are physically and chemically compatible with the remaining components of the composition and especially with the peptide derivatives of general formula (I) contained in the composition of the present invention. Likewise, the nature of said additional ingredients must not unacceptably alter the benefits of the peptide derivatives of the present invention. Said additional ingredients can be synthetic or natural, such as for example plant extracts, or they can come from a biofermentation process. Additional examples are described in the *CTFA Cosmetic Ingredient Handbook, Eleventh Edition* (2006).

An additional aspect of the present invention relates to a cosmetic or pharmaceutical composition containing a cosmetically or pharmaceutically effective amount of at least one peptide derivative of the invention, its stereoisomers, mixtures thereof or its cosmetically or pharmaceutically acceptable salts, and furthermore a cosmetically or pharmaceutically effective amount of at least one extract with defensin synthesis-inducing activity, such as for example and in a non-limiting sense, the extracts or hydrolysates of *Aloe vera, Roast amaranth, Rehmannias radix,* arnica, gardenia, carrot, orange, peach, pineapple, mint, gentian, hibiscus flower, walnut tree leaf, pumpkin, peony, quinoa, boldo, sarsaparilla, sunflower, elderberry, marine alga, corn hydrolysate, soy hydrolysate or rice hydrolysate, among others, and/or furthermore a cosmetically or pharmaceutically effective amount of at least one synthetic compound, extract or product coming from a biofermentation process with defensin expression-stimulating efficacy, such as for example and in a non-limiting sense, isoleucine and its isomers and derivatives, valine and its isomers and derivatives, calcium and its salts, α-MSH and fragments contained in the amino acid sequence of α-MSH, vitamin A and its derivatives and precursors, vitamin D3 and its derivatives, jasmonic acid, fumaric acid, malic acid, citric acid, ascorbic acid, lactic acid, acetic acid, adipic acid, tartaric acid, cinnamic acid, glutamic acid, succinic acid, inulin, alkylglucosides, poly-D-glutamic acid, glycine, L-methionine, L-alanine, L-citrulline, lactoprotein, casein, lactoperoxidase, lysozyme, polyphenol, *Lactobacillus* extract, *fusobacterium* extract or non-photosynthetic, non-fructifying filamentous bacterium, among others.

The cosmetic or pharmaceutical composition of the invention can also additionally contain a cosmetically or pharmaceutically effective amount of at least one bactericidal and/or bacteriostatic agent and/or a fungicidal agent and/or a fungistatic agent, such as for example and in a non-limiting sense, caprylyl glycol, imidazolidinyl urea, methyl 4-hydroxybenzoate [INCI: methylparaben], ethyl 4-hydroxybenzoate [INCI: ethylparaben], propyl 4-hydroxybenzoate [INCI: propylparaben], butyl 4-hydroxybenzoate [INCI: butylparaben], isobutyl 4-hydroxybenzoate [INCI: isobutylparaben], 1,3-bis(hydroxymethyl)-5,5-dimethylimidazolidine-2,4-dione [INCI: DMDM Hydantoin], benzyl 4-hydroxybenzoate [INCI: benzylparaben], benzyl alcohol, dehydroacetic acid, benzoic acid, sorbic acid, salicylic acid, formic acid, propionic acid, 2-bromo-2-nitropropan-1,3-diol, 3-p-chlorophenoxy-1,2-propanediol [INCI: chlorphenesin], dichlorobenzyl alcohol, iodopropynyl butylcarbamate, benzalkonium chloride, benzethonium chloride, chlorhexidine, ethanol, isopropanol, methanol, 1,2-hexanediol, 1,2-octanediol, pentylene glycol, glycerin laurate, glycerin caprylate, glycerin caprate, benzoyl peroxide, chlorhexidine gluconate, triclosan, phenoxyethanol, terpinen-4-ol, α-terpineol, resorcinol, stiemycin, erythromycin, neomycin, clindamycin and their esters, tetracyclines, metronidazole, azelaic acid, tolnaftate, nystatin, clotrimazole, ketoconazole, zinc pyrithione, zinc oxide, isothiazolinones, selenium sulfide, benzylhemiformal, boric acid, sodium borate, 6,6-dibromo-4,4-dichloro-2,2'-methylenediphenol [INCI: bromochlorophene], 5-bromo-5-nitro-1,3-dioxane, tosyl chloramide sodium [INCI: chloramine T], chloroacetamide, p-chloro-m-cresol, 2-benzyl-4-chlorophenol [INCI: chlorophene], dimethyl oxazolidine, dodecyldimethyl-2-phenoxyethyl ammonium bromide [INCI: domiphen bromide], 7-ethylbicyclooxazolidine, glutaraldehyde, N-(4-chlorophenyl)-N-[4-chloro-3-(trifluoromethyl)phenyl]-urea [INCI: cloflucarban], hexetidine, 2-hydroxy-4-isopropyl-2,4, 6-cycloheptatrien-1-one [INCI: Hinokitiol], isopropylmethylphenol, mercury salts, aluminum salts, nysine, phenoxyisopropanol, o-phenylphenol, 3-heptyl-2-[β-heptyl-4-methyl-3H-thiazol-2-ilydene)methyl]-4-methylthiazolium iodide [INCI: Quaternium-73], silver chloride, sodium iodate, thymol, undecylenic acid, diethylenetriaminepentaacetic acid, ethylenediaminetetraacetic acid, lactoperoxidase, glucose oxidase, lactoferrin, and/or a cosmetically or pharmaceutically effective amount of at least one natural extract or essential oil with intrinsic bactericidal, bacteriostatic, fungicidal and/or fungistatic activity, such as for example and in a non-limiting sense, the extracts of *Allium sativum, Calendula officinalis, Chamomilla recutita, Echinacea Purpura, Hyssopus Officinalis, Melaleuca alternifolia* or tea tree oil, among others, for the purpose of combining the bactericidal and/or bacteriostatic effect of β-defensins with the effect of said agents.

Likewise, the cosmetic or pharmaceutical compositions of the present invention can additionally contain a cosmetically or pharmaceutically effective amount of at least one analgesic compound and/or anti-inflammatory compound for the purpose of reducing the swelling and irritation associated to inflammatory processes occurring with microorganism proliferation. Said compounds include synthetic compounds, such as hydrocortisone, clobetasol, dexamethasone, prednisone, paracetamol, acetyl salicylic acid, amoxiprin, benorylate, choline salicylate, diflunisal, faislamine, methyl salicylate, magnesium salicylate, salsalate, diclofenac, aceclofenac, acemetacin, bromfenac, etodolac, indometacin, sulindac, tolmetin, ibuprofen, carprofen, fenbufen, fenoprofen, flurbiprofen, ketoprofen, ketorolac, loxoprofen, naproxen, oxaprozin, tiaprofenic acid, suprofen, mefenamic acid, meclofenamate, meclofenamic acid, nabumetone, phenylbutazone, azapropazone, metamizole, oxyphenbutazone, sulfinpyrazone, piroxicam, lornoxicam, meloxicam, tenoxicam, celecoxib, etoricoxib, lumiracoxib, parecoxib, rofecoxib, valdecoxib, nimesulide, licofelone, omega-3 fatty acids and their biometabolites, morphine, codeine, oxycodone, hydrocodone, diamorphine, petidin, tramadol, brupenorphine, benzocaine, lidocaine, chloroprocaine, tetracaine, procaine, tricyclic antidepressants, amitriptyline, carbamazepine, gabapentin, pregabalin, bisabolol, panthenol, biotin, disodium lauriminodipropionate tocopheryl phosphate, cyclopiroxolamine, nordihydroguaiaretic acid, Q10 co-enzyme or alkylglycerin ethers, or natural extracts or essential oils with intrinsic analgesic and/or anti-inflammatory activity, such as for example and in a non-limiting sense, madecassoside, echinacin, amaranth seed oil, sandalwood oil, placenta extract, peach tree leaf extract, *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Salix alba, Silybum marianum, Tanacetum parthenium* or *Uncaria guianensis*, among others.

Additionally, the present invention relates to a cosmetic or pharmaceutical composition comprising a cosmetically or pharmaceutically effective amount of at least one peptide derivative according to general formula (I), its stereoisomers, mixtures thereof or its cosmetically or pharmaceutically acceptable salts, and furthermore a cosmetically or pharmaceutically effective amount of at least one extract or combination of extracts with healing and/or re-epithelizing activity or effective as coadjuvants in healing and/or re-epithelizing processes, such as for example and in a non-limiting sense, the extracts of *Centella asiatica, Rosa moschata, Echinacea angustifolia, Symphytum officinal, Equisetum arvense, Hypericum perforatum, Mimosa tenuiflora, Aloe vera*, Polyplant® Epithelizing [INCI: *Calendula Officinalis, Hypericum Perforatum, Chamomilla Recutita, Rosmarinus Officinalis*] marketed by Provital, Cytokineol® LS 9028 [INCI: Hydrolyzed Casein, Hydrolyzed Yeast Protein, Lysine HCl] marketed by Laboratories Serobiologiques or Deliner® [INCI: Zea May (Corn) Kernel Extract] marketed by Coletica/Engelhard, among others, and/or furthermore cosmetically or pharmaceutically effective amount of at least one synthetic compound, extract or product coming from a biofermentation process with healing and/or re-epithelizing activity or effective as a coadjuvant in healing and/or re-epithelizing processes, such as for example and in a non-limiting sense, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony stimulating factors, transforming growth factors-beta, tumor necrosis factor-alpha, interferons, interleukins, matrix metalloproteinases, protein tyrosine phosphatase receptors, Antarcticine® [INCI: Pseudoalteromonas Ferment Extract] or Decorinyl® [INCI: Tripeptide-10 Citrulline], marketed by Lipotec, among others.

Applications

Another aspect of the present invention relates to a cosmetic or pharmaceutical method for the treatment and/or care of those conditions, disorders and/or pathologies of mammals, preferably humans, benefiting from a stimulation of endogenous defensin synthesis and/or the cleansing associated to said treatments; comprising the administration of an effective amount of at least one peptide derivative of general formula (I), its stereoisomers, mixtures thereof or its cosmetically or pharmaceutically acceptable salts, preferably in the form of a cosmetic or pharmaceutical composition containing them. The present invention further provides a cosmetic or pharmaceutical method for stimulating the defenses of the organism, preferably the defenses of the skin, mucosae, scalp and/or nails. Likewise, the present invention provides a cosmetic or pharmaceutical method for stimulating the defenses of the skin, mucosae, scalp and/or nails after a surgical intervention, after a treatment with Intense Pulse Light (IPL) therapy, after a treatment with monochromatic pulse light (laser) therapy, after a treatment with chemical desquamating agents or after an overexposure to aggressive external agents, such as for example overexposure to the sun or to extreme cold or to extreme heat.

Likewise, the present invention provides a cosmetic or pharmaceutical method for the treatment and/or care of those conditions, disorders and/or pathologies of the skin, mucosae, scalp and/or nails resulting from microorganism proliferation or being at risk for microorganism proliferation, and/or the cleansing associated to said treatments, comprising the application to the skin, mucosae, scalp and/or nails or the oral or parenteral administration of a cosmetic or pharmaceutical composition containing at least one peptide derivative of the invention, its stereoisomers, mixtures thereof or its cosmetically or pharmaceutically acceptable salts.

Preferably, included among the conditions, disorders and/or pathologies of the skin, mucosae, scalp and/or nails to be treated and/or cared for caused by microorganism proliferation or which are at risk of microorganism proliferation are acne, erysipela, herpes, dandruff, vitiligo, bacterial dermatoses, fungal dermatoses, eczema, sensitive skin, atopic dermatitis, seborrheic dermatitis, diaper rash, genitocrural candidiasis, mucosal candidiasis, such as for example and in a non-limiting sense vaginal candidiasis, interdigital candidiasis or candidiasis associated to diabetes, bacterial vaginosis, impetigo, folliculitis, boils, papulopustular rosacea, paronychia, pityriasis versicolor, staphylococcal scalded skin syndrome, erythrasma, dermatophytosis, such as for example and in a non-limiting sense eczema marginatum of Hebra, ringworm of the scalp, ringworm of the body, ringworm of the foot or athlete's foot, gingivitis, tooth cavities, periodontitis, cutaneous trichosporonosis or white piedra, ungueal mycosis or onychomycosis, infectious complications occurring in the healing processes of ulcers, wounds or burns, ophthalmologic infections, cutaneous disorders resulting from antibiotic treatments or from antifungal treatments, or resulting from occupational exposure or from practicing high-risk sports, or resulting from hormonal deregulations, such as for example pregnancy, or infectious complications occurring in immunosuppressed people, such as for example and in a non-limiting sense people with AIDS or undergoing cancer treatment or in stressful situations, among others, halitosis, bromhidrosis, oily hair and/or scalp, or any other condition, disorder and/or pathology of the skin, mucosae, scalp and/or nails caused by proliferation of *Actinomyces, Aspergillus* spp., *Candida albicans, Clostridium difficile, Clostridium pefringens, Demodex folliculorum, Epidermophyton floccosum, Escherichia coli, Gardnerella vaginalis, Klebsiella* spp., *Malazessia furfur, Mycobacterium* spp., *Peptostreptococcus* spp., *Pityrosporum ovale, Propionibacterium acnes, Pseudomonas aeruginosa, Staphylococcus aureus, Staphylococcus epidermidis, Streptococcus mutans, Streptococcus pyogenes, Streptococcus sanguis, Streptopyogenes, Tinea capitis, Tinea corporis, Trichophyton interdigitale, Trichophyton mentagrophytes, Trichophyton rubrum, Trichophyton yaoundei* or *Trichosporon cutaneum*, among others. Additional examples of microorganisms and conditions, disorders and/or pathologies of the skin, mucosae, scalp and/or nails are described in "*The Skin Microflora and Microbial Skin Disease*", Noble W. C., ed., University of London, Cambridge University Press, UK.

The present invention further provides a cosmetic or pharmaceutical method for preventing or treating infections of the nails and/or cuticles comprising the application to the nails and/or cuticles of a cosmetic or pharmaceutical composition containing at least one peptide derivative of the invention, its stereoisomers, mixtures thereof or its cosmetically or pharmaceutically acceptable salts.

The present invention provides a cosmetic or pharmaceutical method for preventing or treating bromhidrosis comprising the oral or parenteral administration or the application to the areas affected by perspiration, preferably in the axillae, genitalia or feet, of a cosmetic or pharmaceutical composition containing at least one peptide derivative of the invention, its stereoisomers, mixtures thereof or its cosmetically or pharmaceutically acceptable salts.

Likewise, the present invention provides a cosmetic or pharmaceutical method for preventing or treating mucosal infections comprising application to the mucosae or the oral or parenteral administration of a cosmetic or pharmaceutical composition containing at least one peptide derivative of the invention, its stereoisomers, mixtures thereof or its cosmetically or pharmaceutically acceptable salts.

The invention further provides a cosmetic or pharmaceutical method for the treatment of mucosae of the oral cavity or for oral hygiene, comprising the application to the oral cavity or the oral or parenteral administration of a cosmetic or pharmaceutical composition containing at least one peptide derivative of the invention, its stereoisomers, mixtures thereof or its cosmetically or pharmaceutically acceptable salts. Preferably, the composition for oral hygiene is a composition for the treatment or prevention of halitosis, gingivitis and/or periodontitis.

The invention provides a cosmetic or pharmaceutical method for the treatment of vaginal mucosae or for personal hygiene comprising the application to the genitalia or the oral or parenteral administration of a cosmetic or pharmaceutical composition containing at least one peptide derivative of the invention, its stereoisomers, mixtures thereof or its cosmetically or pharmaceutically acceptable salts.

The invention provides a cosmetic or pharmaceutical method for the treatment of ocular mucosae or for ocular hygiene comprising the application to the eyes or the oral or parenteral administration of a cosmetic or pharmaceutical composition containing at least one peptide derivative of the invention, its stereoisomers, mixtures thereof or its cosmetically or pharmaceutically acceptable salts.

The invention further provides a cosmetic or pharmaceutical method for the treatment of the hair and/or scalp or for hair hygiene, preferably for the treatment or the hygiene of oily hair and scalp, for the treatment or hygiene of hair and scalp affected by dandruff or for the treatment or hygiene of seborrheic conditions, comprising the application to the scalp and in the hair or the oral or parenteral administration of a cosmetic or pharmaceutical composition containing at least one peptide derivative of the invention, its stereoisomers, mixtures thereof or its cosmetically or pharmaceutically acceptable salts.

The compositions containing the peptide derivatives of the present invention, their stereoisomers, mixtures thereof or their cosmetically or pharmaceutically acceptable salts can be applied to the skin, mucosae, scalp and/or nails or they can be administered by oral or parenteral route, depending on the requirements for treating a condition, disorder and/or pathology, or they can be administered daily to maintain homeostasis of the microbial flora of the skin, mucosae, scalp and/or nails. Homeostasis of the microbial flora is understood as the auto-regulation of microbial flora levels present in healthy skin, healthy mucosae, healthy scalp or healthy nails, which vary according to the area of the body, ranging between $10^4$ and $10^6$ CFU/cm$^2$ [Selwyn S. (1980) "*Microbiology and ecology of human skin*" *Practitioner* 224:1059-1062], and is basically made up of staphylococci, micrococci and diphtheroids [Noble W. C. and Somerville D. A. in "*Microbiology of Human Skin*" 1974, W.B. Saunders Company Ltd., ed, London, UK].

The application or administration frequency may vary widely, depending on the needs of each subject, an application or administration range from once a month to ten times a day being suggested, preferably from once a week to four times a day, more preferably from three times a week to three times a day, still more preferably one or two times a day.

An additional aspect of the present invention relates to the use of at least one of the peptide derivatives of general formula (I), its stereoisomers, mixtures thereof or its cosmetically or pharmaceutically acceptable salts in the preparation of a cosmetic or pharmaceutical composition for the treatment, care and/or cleansing of the skin, mucosae, scalp and/or nails.

The present invention additionally relates to the use of at least one of the peptide derivatives of general formula (I), its stereoisomers, mixtures thereof or its cosmetically or pharmaceutically acceptable salts in the preparation of a cosmetic or pharmaceutical composition for the stimulation of the defenses of the organism, preferably the defenses of the skin, mucosae, scalp and/or nails. Preferably, the stimulation of the defenses of the organism is mediated by the induction of endogenous β-defensin expression, and more preferably by the induction of human β-defensin-2 and/or β-defensin-3 expression.

The present invention additionally relates to the use of at least one of the peptide derivatives of general formula (I), its stereoisomers, mixtures thereof or its cosmetically or pharmaceutically acceptable salts in the preparation of a cosmetic or pharmaceutical composition for stimulating defenses of the skin, mucosae, scalp and/or nails after a surgical intervention, after a treatment with Intense Pulse Light (IPL) therapy, after a treatment with monochromatic pulse light (laser) therapy, after a treatment with chemical desquamating agents or after overexposure to aggressive external agents, such as for example overexposure to the sun or to extreme cold or extreme heat.

Likewise, another aspect of the present invention relates to the use of at least one of the peptide derivatives of general formula (I), its stereoisomers, mixtures thereof or its cosmetically or pharmaceutically acceptable salts in the preparation of a cosmetic or pharmaceutical composition for the treatment, care and/or cleansing of those conditions, disorders and/or pathologies of the skin, mucosae, scalp and/or nails resulting from microorganism proliferation or being at risk for microorganism proliferation. Preferably, the cosmetic or pharmaceutical compositions are prepared to treat, care and/or cleanse those areas of the skin, mucosae, scalp and/or nails affected by acne, erysipela, herpes, dandruff, vitiligo, bacterial dermatoses, fungal dermatoses, eczema, sensitive skin, atopic dermatitis, seborrheic dermatitis, diaper rash or genitocrural candidiasis, mucosal candidiasis, such as for example and in a non-limiting sense vaginal candidiasis, interdigital candidiasis or candidiasis associated to diabetes, bacterial vaginosis, impetigo, folliculitis, boils, papulopustular rosacea, paronychia, pityriasis versicolor, staphylococcal scalded skin syndrome, erythrasma, dermatophytosis, such as for example and in a non-limiting sense eczema marginatum of Hebra, ringworm of the scalp, ringworm of the body, ringworm of the foot or athlete's foot, gingivitis, tooth cavities, periodontitis, cutaneous trichosporonosis or white piedra, ungueal mycosis or onychomycosis, infectious complications occurring in the healing processes of ulcers, wounds or burns, ophthalmologic infections, cutaneous disorders resulting from antibiotic treatments or from antifungal treatments, or resulting from occupational exposure or from practicing high-risk sports, or resulting from hormonal deregulations, such as for example pregnancy, or infectious complications occurring in immunosuppressed people, such as for example and in a non-limiting sense people with AIDS or undergoing cancer treatment or in stressful situations, among others, halitosis, bromhidrosis, oily hair and/or scalp, or any other condition, disorder and/or pathology of the skin, mucosae, scalp and/or nails caused by proliferation of *Actinomyces, Aspergillus* spp., *Candida albicans, Clostridium difficile, Clostridium pefringens, Demodex folliculorum, Epidermophyton floccosum, Escherichia coli, Gardnerella vaginalis, Klebsiella* spp., *Malazessia furfur, Mycobacterium* spp., *Peptostreptococcus* spp., *Pityrosporum ovale, Propionibacterium acnes, Pseudomonas aeruginosa, Staphylococcus aureus, Staphylococcus epidermidis, Streptococcus mutans, Streptococcus pyogenes, Streptococcus sanguis, Streptopyogenes, Tinea capitis, Tinea corporis, Trichophyton interdigitale, Trichophyton mentagrophytes, Trichophyton rubrum, Trichophyton yaoundei* or *Trichosporon cutaneum*, among others.

In an additional embodiment, the present invention relates to the use of at least one of the peptide derivatives of general formula (I), its stereoisomers, mixtures thereof, or its cosmetically or pharmaceutically acceptable salts in the preparation of a cosmetic or pharmaceutical composition for preventing or treating infections of the nails and/or cuticles.

According to another embodiment, the peptide derivatives of general formula (I), their stereoisomers, mixtures thereof or their cosmetically or pharmaceutically acceptable salts are used in the preparation of a cosmetic or pharmaceutical composition for preventing or treating infections of the mucosae, preferably infections of the mucosae of the oral cavity, such as for example and in a non-limiting sense gingivitis or periodontitis, or infections of the vaginal mucosae, such as for example and in a non-limiting sense vaginal candidiasis or bacterial vaginosis.

In another additional embodiment, the present invention relates to the use of at least one of the peptide derivatives of general formula (I), its stereoisomers, or its cosmetically or pharmaceutically acceptable salts in the preparation of a cosmetic or pharmaceutical composition for oral hygiene. Preferably, the cosmetic or pharmaceutical composition is used for the treatment or prevention of halitosis, gingivitis and periodontitis. Examples of a cosmetic or pharmaceutical composition for oral hygiene include toothpastes, mouthwashes for rinsing the mouth or chewing gum, among others.

An additional aspect of the present invention relates to the use of at least one of the peptide derivatives of general formula (I), its stereoisomers, mixtures thereof, or its cosmetically or pharmaceutically acceptable salts in the preparation of a cosmetic or pharmaceutical composition for body hygiene, for personal hygiene or hair hygiene.

Preferably, the cosmetic or pharmaceutical compositions for hair hygiene are selected from the group consisting of compositions for the hygiene of oily hair or scalp, compositions for the treatment or prevention of dandruff and compositions for the hygiene of seborrheic conditions. Examples of a cosmetic or pharmaceutical composition for hair hygiene include shampoos, hair lotions, hair tonics or conditioners for the scalp, among others. Preferably, the cosmetic or pharmaceutical compositions for body hygiene are selected from the group consisting of compositions for the hygiene of oily skin. Examples of a cosmetic or pharmaceutical composition for body hygiene include soaps, shower gels, facial cleansing gels, antibacterial after-shave gels, body or facial milks, astringent lotions or creams for oily skin. Examples of a cosmetic or pharmaceutical composition for personal hygiene include personal hygiene soaps or gels.

An additional embodiment of the present invention relates to the use of at least one of the peptide derivatives of general formula (I), its stereoisomers, mixtures thereof, or its cosmetically or pharmaceutically acceptable salts in the preparation of a cosmetic or pharmaceutical composition for treating, reducing and/or preventing bromhidrosis. Examples of a cosmetic or pharmaceutical composition for the treatment, prevention and/or reduction of bromhidrosis include deodorants and antiperspirants.

The following specific examples provided herein serve to illustrate the nature of the present invention. These examples are included only for illustrative purposes and must not be interpreted as limitations to the invention herein claimed.

EXAMPLES

General Methodology

All the reagents and solvents are of a quality for synthesis and are used without any additional treatment.

Abbreviations

The abbreviations used for the amino acids follow the rules of the IUPAC-IUB Commission on Biochemical Nomenclature specified in *Eur. J. Biochem.* (1984) 138, 9-37 and in *J. Biol. Chem.* (1989) 264, 633-673.

Ac, acetyl; DNA, deoxyribonucleic acid; Ahx, ε-aminohexanoic or 6-aminocaproic acid; All, allyl; Alloc, allyloxycarbonyl; Ala, alanine; AM, 2-[4-aminomethyl-(2,4-dimethoxyphenyl)]-phenoxyacetic acid; Arg, arginine; RNA, ribonucleic acid; mRNA, messenger ribonucleic acid; Boc, tert-butyloxycarbonyl; Bzl, benzyl; Cbz, benzyloxycarbonyl; CFU, colony forming units; cHex, cyclohexyl; ClTrt, 2-chlorotrityl resin; DCM, dichloromethane; DIEA, N,N-diisopropylethylamine; DIPCDI, N,N'-diisopropylcarbodiimide; DMEM, Dulbecco's Modified Eagle's Medium; DMF, N,N-dimethylformamide; DPPC, dipalmitoylphosphatidylcholine; EDTA, ethylenediaminetetraacetic acid; equiv, equivalent; ESI-MS, electrospray ionization mass spectrometry; FBS, fetal bovine serum; Fmoc, 9-fluorenylmethyloxycarbonyl; G418, geneticin; Glu, glutamic acid; hBD, human β-defensins; HNP, human α-defensins; HOAt, 1-hydroxyazabenzotriazole; HOBt, 1-hydroxybenzotriazole; HPLC, high performance liquid chromatography; Ile, isoleucine; INCI, International Nomenclature of Cosmetic Ingredients; IPL, intense pulse light; LPS, Pseudomona aeruginosa lipopolysaccharide; MBHA, p-methylbenzhydrylamine resin; MeCN, acetonitrile; MeOH, methanol; Met, methionine; mLV, multilaminar vesicles; MSH, melanocyte-stimulating hormone; Mtr, 4-methoxy-2,3,6-trimethylbenzenesulfonyl; NMP, N-methylpyrrolidone; PAL, 5-(4-aminomethyl-3,5-dimethoxyphenoxy)valeric acid; Palm, palmitoyl; Pbf, 2,2,4,6,7-pentamethyldihydrobenzofuran-5-sulfonyl; Phg, phenylglycine; Pmc, 2,2,5,7,8-pentamethylchroman-6-sulfonyl;®, resin; RPMI-1640, Roswell Park Memorial Institute medium; RT-PCR, Reverse Transcription Polymerase Chain Reaction; AIDS, acquired immunodeficiency syndrome; spp., species; tBu, tert-butyl; Teoc, 2-(trimethylsilyl)ethyloxycarbonyl; TFA, trifluoroacetic acid; THF, tetrahydrofuran; TIS, triisopropylsilane; Tos, para-toluenesulfonyl or tosyl; Troc, 2,2,2-trichloroethyloxycarbonyl; Trt, triphenylmethyl or trityl; ULAs, units of luminescence absorption; ULV, unilaminar vesicles; UV, ultraviolet.

Chemical Synthesis

All the synthetic processes are carried out in polypropylene syringes equipped with porous polyethylene discs, in Pyrex reactors equipped with a porous plate, or in an ACT39652 automatic synthesizer (Advanced Chemtech, Inc). The soluble solvents and reagents are eliminated by suction. The elimination of the Fmoc group is carried out with piperidine-DMF (2:8, v/v) (1×1 min, 1×5 min; 5 mL/g resin) [Lloyd-Williams P., Albericio F. and Giralt, E. (1997) "*Chemical Approaches to the Synthesis of Peptides and Proteins*" CRC, Boca Raton, Fla., USA]. The washings between the steps of deprotecting, coupling and again deprotecting were carried out with DMF (3×1 min) using 10 mL solvent/g resin each time. The coupling reactions were carried out with 3 mL solvent/g resin. The control of the couplings is carried out by means of the ninhydrin test [Kaiser E., Colescott R. L., Bossinger C. D. and Cook P. I. (1970) "*Color test for detection of free terminal amino groups in the solid-phase synthesis of peptides*" Anal. Biochem. 34:595-598]. All the synthetic transformations and washings were carried out at room temperature.

Example 1

General Process for Synthesizing Peptidyl-Resins

Synthesis of Fmoc-AA$^1$-AA$^2$-AA$^3$-AA$^4$-O-2-ClTrt-® and Fmoc-AA$^1$-AA$^2$-AA$^3$-AA$^4$-AM-MBHA-®.

250 mg of the commercial resins H-L-Ile-O-2-ClTrt-®, H-L-Ala-O-2-ClTrt-®, H-L-Phg-O-2-ClTrt-®, H-D-Phg-O-2-ClTrt-® and Fmoc-AM-MBHA-®, were weighed and distributed in 12, 6, 6, 6 and 24 wells respectively, of the 96-position reactor of an ACT396Ω multiple synthesizer. The synthesis of the peptides was programmed through the Advanced Chemtech v. 1.36.03 commercial software. A stock solution of each of the amino acids Fmoc-Ahx-OH, Fmoc-L-Ala-OH, Fmoc-D-Ala-OH, Fmoc-L-Arg(Pbf)-OH, Fmoc-D-Arg(Pbf)-OH, Fmoc-L-Glu(OtBu)-OH, Fmoc-D-Glu(OtBu)-OH, Fmoc-L-Ile-OH, Fmoc-D-Ile-OH, Fmoc-L-Met-OH, Fmoc-D-Met-OH, Fmoc-L-Phg-OH and Fmoc-D-Phg-OH was prepared in DMF at a concentration of 0.5 M containing 0.5 M HOBt, as well as a 1 mM DIPCDI solution and a 20% piperidine solution in DMF. In each case, the cycles of incorporation of each amino acid were programmed with the following sequence: washings (DMF, 3×2 min), deprotection (20% piperidine in DMF, 1×5 min+1×20 min), washings (DMF, 3×2 min), coupling of the desired amino acid (5 equiv Fmoc-amino acid, 5 equiv DIPCDI, 60 min) and washings (DMF, 3×2 min).

Once the synthesis had ended, the peptidyl-resins were washed with DCM (5×3 min) and dried by nitrogen stream.

Example 2

General Process for Cleaving the N-Terminal Fmoc protective group

Synthesis of H-AA$^1$-AA$^2$-AA$^3$-AA$^4$-O-2-ClTrt-® and H-AA$^1$-AA$^2$-AA$^3$-AA$^4$-AM-MBHA-®.

50 mg of the peptidyl-resins obtained in Example 1 were aliquoted and the N-terminal Fmoc group was deprotected as described in the general methods (20% piperidine in DMF, 1×5 min+1×20 min). The peptidyl-resins were washed with DMF (5×1 min), DCM (4×1 min), diethyl ether (4×1 min) and vacuum-dried.

Example 3

Process for Introducing the Palmitoyl R$^1$ Group

Synthesis of Palm-AA$^1$-AA$^2$-AA$^3$-AA$^4$-O-2-ClTrt-® and Palm-AA$^1$-AA$^2$-AA$^3$-AA$^4$-AM-MBHA-®.

10 equiv of palmitic acid predissolved in 1 mL of DMF, in the presence of 10 equiv of HOBt and 10 equiv of DIPCDI, were incorporated on 50 mg of the peptidyl-resins obtained in Example 1, the N-terminal Fmoc group being previously deprotected as described in the general methods. They were allowed to react for 15 h, after which the peptidyl-resins were washed with THF (5×1 min), DCM (5×1 min), DMF (5×1 min), MeOH (5×1 min), DMF (5×1 min), THF (5×1 min), DMF (5×1 min), DCM (4×1 min), ether (3×1 min), and vacuum-dried.

Example 4

Process for Introducing the Acetyl $R^1$ Group

Synthesis of Ac-AA$^1$-AA$^2$-AA$^3$-AA$^4$-O-2-ClTrt-® and Ac-AA$^1$-AA$^2$-AA$^3$-AA$^4$-AM-MBHA-®.

50 mg of the peptidyl-resins obtained in Example 1, the N-terminal Fmoc group being previously deprotected as described in the general methods, were treated with 25 equiv of acetic anhydride in the presence of 25 equiv of DIEA using 0.5 mL of DMF as a solvent. They were allowed to react for 30 min, after that the peptidyl-resins were washed with DMF (5×1 min), DCM (4×1 min), diethyl ether (4×1 min) and vacuum-dried.

Example 5

Process for Cleaving from the Polymeric Support

Obtaining H-AA$^1$-AA$^2$-AA$^3$-AA$^4$-OH, Ac-AA$^1$-AA$^2$-AA$^3$-AA$^4$-OH, Palm-AA$^1$-AA$^2$-AA$^3$-AA$^4$-OH, H-AA$^1$-AA$^2$-AA$^3$-AA$^4$-NH$_2$, Ac-AA$^1$-AA$^2$-AA$^3$-AA$^4$-NH$_2$ and Palm-AA$^1$-AA$^2$-AA$^3$-AA$^4$-NH$_2$.

25 mg of the dried peptidyl-resins obtained in Examples 2, 3 and 4 were treated with 0.5 mL of TFA-TIS-H$_2$O (90:5:5) for 2 h at room temperature with stirring. The filtrates were collected on 10 mL of cold diethyl ether, filtered through polypropylene syringes equipped with porous polyethylene discs and washed 5 times with 10 mL of diethyl ether. The final precipitates were vacuum-dried.

The HPLC analysis of the peptides obtained in gradients of MeCN (+0.07% TFA) in H$_2$O (+0.1% TFA) showed purity greater than 80% in all the cases. The identity of the peptides obtained was confirmed by ES-MS. The same procedure could have been applied to the peptidyl resins H-AA$^1$-AA$^2$-AA$^3$-AA$^4$-AM-MBHA-® obtained in Example 2 to obtain H-AA$^1$-AA$^2$-AA$^3$-AA$^4$-NH$_2$.

Example 6

Prophetic—Process for Cleaving from the Polymeric Support and Functionalizing with Substituted Amine $R_2$ Obtaining Ac-AA$^1$-AA$^2$-AA$^3$-AA$^4$-NH—(CH$_2$)$_{15}$—CH$_3$.

The peptide derivatives Ac-AA$^1$-AA$^2$-AA$^3$-AA$^4$-OH with the side chains completely protected were obtained by treatment of the peptidyl-resins Ac-AA$^1$-AA$^2$-AA$^3$-AA$^4$-O-2-ClTrt-® of Example 4, previously vacuum-dried in the presence of KOH, with a 3% solution of TFA in DCM for 5 minutes. The filtrates were collected on cold diethyl ether and the treatment was repeated three times. The ether solutions were evaporated in vacuum to dryness and at room temperature, the precipitates were resuspended in 50% MeCN in H$_2$O and lyophilized. 10 mg of the crude products obtained are weighed in a flask, 3 equiv of hexadecylamine and 25 mL of anhydrous DMF are added. 2 equiv of DIPCDI are added, and allowed to react with magnetic stirring at 47° C. The reactions are controlled by means of HPLC by the disappearance of the initial products, being complete after 24-48 h. The solvents are evaporated to dryness and coevaporated twice with DCM. The residues obtained [Ac-AA$^1$-AA$^2$-AA$^3$-AA$^4$-NH—(CH$_2$)$_9$—CH$_3$ with the side chains completely protected] are resuspended in 25 mL of a mixture of TFA-DCM-anisole (49:49:2) and allowed to react for 30 min at room temperature. 250 mL of cold diethyl ether are added, the solvents are evaporated under reduced pressure and two additional coevaporations with ether are carried out. The residues are dissolved in a mixture of 50% MeCN in H$_2$O and lyophilized.

The HPLC analysis of the peptide derivatives obtained in gradients of MeCN (+0.07% TFA) in H$_2$O (+0.1% TFA) showed purity greater than 80% in all the cases.

Example 7

Prophetic

Composition of a face cream containing Ac-L-Arg-Ahx-L-Ala-OH.

| INGREDIENT (INCI Nomenclature) | % BY WEIGHT |
|---|---|
| A *BUTYROSPERMUM PARKII* | 3.5-4.5 |
| A CETEARYL ETHYLHEXANOATE | 3-5 |
| A GLYCERYL STEARATE S.E. | 1.5-2.5 |
| A SQUALANE | 0.5-1 |
| A PEG-100 STEARATE | 1 |
| A POLYSORBATE 60 | 0.30 |
| A CETYL PALMITATE | 1.5-2.5 |
| A DIMETHICONE | 2.5-3.5 |
| A CETEARYL ALCOHOL | 1.5-2.5 |
| A PALMITIC ACID | 0.5 |
| B AQUA (WATER) | 2 |
| B GLYCERIN | 1.5-2.5 |
| E PRESERVATIVES | q.s. |
| F Ac-L-Arg-Ahx-L-Ala-OH | 0.10 |
| F AQUA (WATER) | q.s. 100 |
| B BUTYLENE GLYCOL | 1-3 |
| B MANNITOL | 0.5-1.5 |
| B HYDROGENATED LECITHIN | 0.5-1.5 |
| B PROPYLENE GLYCOL | 0.5-1.5 |
| C CARBOMER | 0.4 |
| C ETHYLHEXYL PALMITATE | 1.5-2.5 |
| D TROMETHAMINE | 0.4 |
| D AQUA (WATER) | 1 |

Preparation

Mix the components of Phase A and heat at 70° C.

Mix the components of Phase B and heat at 70° C.

Add Phase C on Phase B stirring with a homogenizer (Silverson) for 5 minutes.

On the mixture of Phases B and C, gradually add Phase A with a homogenizer and maintain the homogenization for 15 minutes.

Start the cooling to 30-35° C. with gentle stirring. Add Phase D at 50° C. Maintain the stirring. Add the previously solubilized Phases E and F at 35-38° C.

Example 8

Prophetic

Preparation and composition of liposomes containing Ac-L-Glu-L-Met-L-Ala-L-Ile-OH (Ac-SEQ ID No. 3-OH).

Dipalmitoylphosphatidylcholine (DPPC) is weighed and dissolved in chloroform. The solvent is evaporated under reduced pressure until obtaining a thin phospholipid layer, and this layer is hydrated by treatment at 55° C. with an aqueous solution of the peptide derivative at the desired concentration (containing)Phenonip®, obtaining MLV liposomes. ULV liposomes are obtained by submerging the MLV liposomes in an ultrasound bath at 55° C. for 8 cycles of 2 min in intervals of 5 min. The size of the liposomes ULV is reduced by passing them through an extrusion system under high pressure.

| INGREDIENT (INCI Nomenclature) | % BY WEIGHT |
|---|---|
| DIPALMITOYLPHOSPHATIDYLCHOLINE | 4.0 |
| Ac-L-Glu-L-Met-L-Ala-L-Ile-OH (Ac-SEQ ID No. 3-OH) | 0.2 |
| PHENOXYETHANOL, METHYLPARABEN, ETHYLPARABEN, BUTYLPARABEN, PROPYLPARABEN, ISOBUTYLPARABEN | 0.5 |
| AQUA (WATER) | q.s. 100 |

Example 9

Prophetic

Preparation of a composition in the form of liposome gel containing Ac-L-Glu-L-Met-L-Ala-L-Ile-OH (Ac-SEQ ID No. 3-OH).

The liposomes of prophetic Example 8 are dispersed in water with preservatives (EDTA, imidazolidinyl urea and Phenonip®) under gentle stirring. Hispagel® 200 [INCI: Aqua, glycerin and glyceryl polyacrylate] is added and stirred gently until a homogeneous mixture is obtained.

| INGREDIENT (INCI Nomenclature) | % BY WEIGHT |
|---|---|
| LIPOSOMES CONTAINING Ac-L-Glu-L-Met-L-Ala-L-Ile-OH (1%) (Ac-SEQ ID No. 3-OH) | 10.00 |
| DISODIUM EDTA | 0.15 |
| IMIDAZOLIDINYL UREA | 0.10 |
| PHENOXYETHANOL, METHYLPARABEN, ETHYLPARABEN, BUTYLPARABEN, PROPYLPARABEN, ISOBUTYLPARABEN | 0.50 |
| AQUA (WATER) | 29.25 |
| AQUA (WATER), GLYCERIN, GLYCERYL POLYACRYLATE | 60.00 |

Example 10

Prophetic

Composition for the treatment of nails containing Palm-L-Arg-Ahx-L-Ala-OH.

| INGREDIENT (INCI Nomenclature) | % BY WEIGHT |
|---|---|
| A CETEARYL ALCOHOL/SODIUM CETEARYL SULFATE | 10 |
| A *PRUNUS DULCIS* | 0.05 |
| A *BUTYROSPERMUM PARKII* | 0.5 |
| A ZINC OXIDE | 0.5 |
| A TOCOPHERYL ACETATE | 0.1 |
| A METHYL PARABEN | 0.1-0.3 |
| B GLYCERIN | 13 |
| B AQUA (WATER) | 10 |
| B HYDROLYZED SOY PROTEIN | 0.1 |
| C Palm-L-Arg-Ahx-L-Ala-OH | 0.1 |
| C AQUA (WATER) | q.s. 100 |

Preparation

Mix the components of Phase A and heat at 70° C.

Mix the components of Phase B and heat at 70° C.

Add Phase A on Phase B stirring with a homogenizer (Silverson) for 5 minutes and maintain the homogenization for 15 minutes.

Start the cooling to 30-35° C. with gentle stirring. Add the previously solubilized Phase C at 35-38° C.

Example 11

Prophetic

Composition of a body lotion containing Palm-L-Arg-Ahx-L-Ala-NH$_2$.

| INGREDIENT (INCI Nomenclature) | % BY WEIGHT |
|---|---|
| A CETEARYL ETHYLHEXANOATE | 3-5 |
| A GLYCERYL STEARATE SE. | 2.5 |
| A PEG-100 STEARATE | 1 |
| A SQUALANE | 2 |
| A DIMETHICONE | 0.5-1 |
| A CETYL ALCOHOL | 0.4-0.8 |
| B AQUA (WATER) | 1 |
| B BUTYLENE GLYCOL | 1-3 |
| B GLYCERIN | 0.5-2 |
| B PROPYLENE GLYCOL | 0.5-1.5 |
| C CARBOMER | 0.2 |
| C ETHYLHEXYL PALMITATE | 0.5-1.5 |
| C ACRYLATES/C10-30 ALKYL ACRYLATE CROSSPOLYMER | 0.1 |
| D AQUA (WATER) | 1 |
| D TROMETHAMINE | 0.25 |
| E PRESERVATIVES | q.s. |
| F Palm-L-Arg-Ahx-L-Ala-NH$_2$ | 0.10 |
| F AQUA (WATER) | q.s. 100 |

Preparation

Mix the components of Phase A and heat at 70° C.

Mix the components of Phase B and heat at 70° C.

Add Phase C on Phase B stirring with a homogenizer (Silverson) for 5 minutes.

On the mixture of Phases B and C, gradually add Phase A with a homogenizer and maintain the homogenization for 15 minutes.

Start the cooling to 30-35° C. with gentle stirring. Add Phase D at 50° C. Maintain the stirring. Add the previously solubilized Phases E and F at 35-38° C.

Example 12

Prophetic

Composition of a hair lotion containing Ac-L-Arg-Phg-Phg-NH—(CH$_2$)$_{1-5}$—CH$_3$.

| INGREDIENT (INCI Nomenclature) | % BY WEIGHT |
|---|---|
| A ALCOHOL DENAT. | 50-60 |
| A PANTHENOL | 0.05-0.15 |
| A ZINC RICINOLEATE | 0.05-0.10 |
| A FRAGRANCE | 0.02 |
| B AQUA (WATER) | q.s. 100 |
| B Ac-L-Arg-Phg-Phg-NH—(CH$_2$)$_{15}$—CH$_3$ | 0.01 |

Preparation

Mix the components of Phase A.

Mix the components of Phase B.

Slowly add Phase B on Phase A with stirring until complete homogenization.

Example 13

Prophetic

Composition of a mouthwash containing Ac-L-Arg-Phg-Phg-OH.

| INGREDIENT (INCI Nomenclature) | % BY WEIGHT |
| --- | --- |
| Ac-L-Arg-Phg-Phg-OH | 0.10 |
| SODIUM SACCARIN | 0.01-0.03 |
| SORBITOL | 4-6 |
| PROPYLENE GLYCOL | 8-12 |
| PEG-60 HYDROGENATED CASTOR OIL | 1-3 |
| AQUA (WATER) | q.s. 100 |

Preparation

Mix the components until complete homogenization.

Example 14

Assay of activation of the hBD2 promoter in a stable cell line by the compounds of general formula (I) obtained in Example 5.

The A549 human epithelial cell line was cultured using RPMI-1640 medium supplemented with FBS and Penicillin-Streptomycin. It was routinely cultured by dividing the cultures twice a week at a 1:10 dilution using Trypsin-EDTA. $10^6$ cells of the A549 line were seeded in a 60 mm disc treated with polylysine. After 24 h they were cotransfected with 10 μg of a gene construct formed by the hBD2 gene promoter followed by the luciferase protein gene (pGL3-hBD2promotor-Luc), and the pcDNA3B plasmid DNA containing the geneticin antibiotic resistance gene, at a 1:5 pcDNA3B.1/pGL3-hBD2promotor-Luc ratio. 25 μL of Lipofectamine™ 2000 were used for the transfection. After 24 h the selection was started with complete medium supplemented with the G418-Geneticin® antibiotic, the selection medium being renewed every 2 days. Different clones were isolated, which were characterized and selected based on the luciferase activity.

The selected stable lines were cultured using complete medium for the parental line supplemented with G418. They were routinely cultured by dividing the cultures twice a week at a 1:10 dilution using Trypsin-EDTA.

The capacity to activate the hBD2 promoter was determined by means of the luciferase activity assay since a transcriptional agent inducing hBD2 synthesis causes luciferase enzyme production by means of activating the hBD2 gene promoter contained in the pGL3-hBD2promotor-Luc construct, a luminescence increase being observed. The selected stable cell lines were seeded at 20,000 cells per plate. After 24 h the plates were washed and incubated for 24 h in modified RPMI-1640 medium without L-Isoleucine with different peptide derivatives at a concentration of 0.5 mM. LPS (100 μg/mL) and L-Isoleucine (25 μg/mL) were used as positive controls with the same treatment as the peptide derivatives. Once the incubation period had ended, the *Steady-Glo Luciferase Assay System* reagent (Promega Corp.) was added to the cells, following the protocol of the commercial company. The luminescent signal (ULAs/s) produced by the reaction between the luciferase and its substrate was quantified with a LUMIstar Galaxy plate luminometer (BMG Labtechnologies). Based on the values of luciferase activity (ULAs/s), standardized with the negative controls, the activation of the hBD2 promoter was determined. Table 2 details the activity of the compounds of general formula (I) which showed a luminescence increase equal to or greater than 20%.

TABLE 2

| COMPOUND | LUMINESCENCE INCREASE |
| --- | --- |
| CONTROL | 100% |
| LPS | 185% |
| L-Ile | 127% |
| Ac-L-Arg-Phg-Phg-OH | 120% |
| H-L-Glu-L-Met-L-Ala-L-Ile-OH (H-SEQ ID No. 3-OH) | 125% |
| Ac-L-Arg-Ahx-L-Ala-OH | 137% |
| Palm-L-Glu-L-Met-L-Ala-L-Ile-NH$_2$ (Palm-SEQ ID No. 3-NH$_2$) | 137% |
| Ac-L-Glu-L-Met-L-Ala-L-Ile-OH (Ac-SEQ ID No. 3-OH) | 196% |

Example 15

Quantification of the hBD2 mRNA secreted in human keratinocytes after incubation with Ac-L-Glu-L-Met-L-Ala-L-Ile-OH (Ac-SEQ ID No. 3-OH), Ac-L-Arg-Phg-Phg-OH and Ac-L-Arg-Ahx-L-Ala-OH.

The quantification of the amount of mRNA secreted was carried out by means of a real-time quantitative RT-PCR assay. $3\times10^6$ cells of a human keratinocyte line were used, seeded in 25 cm$^2$ flasks. The cells were washed and incubated for 16 h-24 h with different peptide derivatives at a concentration of 1 mm or 0.25 mm in a volume of 3 mL of DMEM medium. LPS (100 μg/mL) and L-Ile (200 μg/mL) were used as positive controls. The supernatants of the cells were stored at −80° C., to analyze the secreted hBD2 protein level and the total RNA was extracted from the cells with the RNeasy kit (Quiagen) following the protocol of the commercial company.

A retrotranscription reaction was carried out in a Mastercycler thermal cycler from 1 μg of total RNA of each sample, using the GeneAmp RNA PCR kit (Applied Biosystems) according to the protocol of the commercial company, and subsequently a real-time PCR was carried out by means of the assay with the SYBR Green I fluorophore in an ABI PRIS M 7700 Sequence Detector (Applied Biosystems).

The amount of mRNA was quantified by standardizing normalizing it with respect to the values of endogenous 18S ribosomal RNA. These values were in turn standardized with respect to the untreated cells and they were represented as the relative hBD2 mRNA level.

TABLE 3

| COMPOUND | Relative hBD2 mRNA level |
| --- | --- |
| CONTROL | 100% |
| LPS | 192% |
| L-Ile | 125% |
| 1 mm Ac-L-Glu-L-Met-L-Ala-L-Ile-OH (Ac-SEQ ID No. 3-OH) | 323% |
| 0.25 mm Ac-L-Arg-Ahx-L-Ala-OH | 126% |
| 0.25 mm Ac-L-Arg-Phg-Phg-OH | 201% |

Example 16

Quantification of the hBD2 secreted in human keratinocytes after incubation with Ac-L-Glu-L-Met-L-Ala-L-Ile-OH (Ac-SEQ ID No. 3-OH), Ac-L-Arg-Phg-Phg-OH and Ac-L-Arg-Ahx-L-Ala-OH.

The amount of hBD2 secreted by human keratinocytes was quantified by means of an ELISA assay using the Human BD-2 ELISA Development commercial kit (Peprotech) from the supernatants of the cells coming from Example 15.

Based on the absorbance data obtained, the hBD2 protein level was calculated after the calibration with recombinant hBD2. The values of hBD2 obtained were standardized with respect to the values of the control assays (untreated cells).

TABLE 4

| COMPOUND | Relative hBD2 level |
| --- | --- |
| CONTROL | 100% |
| LPS | 143% |
| L-Ile | 134% |
| 1 mm Ac-L-Glu-L-Met-L-Ala-L-Ile-OH (Ac-SEQ ID No. 3-OH) | 129% |
| 0.25 mm Ac-L-Arg-Ahx-L-Ala-OH | 126% |
| 0.25 mm Ac-L-Arg-Phg-Phg-OH | 116% |

The invention claimed is:

1. A peptide of the general formula (I)

$$R^1\text{-}AA^1\text{-}AA^2\text{-}AA^3\text{-}AA^4\text{-}R^2 \quad (I)$$

its stereoisomers, or its cosmetically or pharmaceutically acceptable salt, wherein:

$AA^1$ is selected from the group consisting of -Glu- and -Arg-;

$AA^2$ is selected from the group consisting of -Met-, -Ahx- and -Phg-;

$AA^3$ is selected from the group consisting of -Ala- and -Phg-;

$AA^4$ is selected from the group consisting of -Ile- or a single bond;

$R^1$ is selected from the group consisting of H, substituted non-cyclic aliphatic group selected from the group consisting of acetyl, tert-butanoyl, hexanoyl, 2-methylhexanoyl, octanoyl, decanoyl, lauroyl, myristoyl, palmitoyl, stearoyl, oleoyl, and linoleoyl, non-substituted non-cyclic aliphatic group, substituted or non-substituted alicyclyl, non-substituted heterocyclyl, non-substituted heteroarylalkyl, substituted or non-substituted aryl, non-substituted aralkyl and $R^5$—C(O)—; and $R^2$ is selected from the group consisting of —$NR^3R^4$, —$OR^3$ and —$SR^3$;

wherein $R^3$ and $R^4$ are independently selected from the group consisting of H, non-substituted non-cyclic aliphatic group, substituted or non-substituted alicyclyl, heterocyclyl, non-substituted heteroarylalkyl, substituted or non-substituted aryl, and non-substituted aralkyl;

wherein $R^5$ is selected from the group consisting of H, non-substituted non-cyclic aliphatic group, substituted or non-substituted alicyclyl, substituted or non-substituted aryl, non-substituted aralkyl, substituted or non-substituted heterocyclyl, and non-substituted heteroarylalkyl.

2. The peptide according to claim 1, wherein $R^1$ is H or a $R^5$—C(O)— group, wherein $R^5$ is selected from the group consisting of non-substituted $C_1$-$C_{24}$ alkyl, non-substituted $C_2$-$C_{24}$ alkenyl, non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, non-substituted $C_7$-$C_{24}$ aralkyl, non-substituted 3-10 member ring heterocyclyl, and heteroarylalkyl having an alkyl chain of 1 to 3 carbon atoms and a non-substituted aromatic heterocyclyl group with from 2 to 24 carbon atoms and from 1 to 3 atoms different from carbon or hydrogen.

3. The peptide according to claim 1, wherein $R^2$ is —$NR^3R'$, —$OR^3$ or —$SR^3$, wherein $R^3$ and $R^4$ are independently selected from the group consisting of H, non-substituted $C_1$-$C_{24}$ alkyl, non-substituted $C_2$-$C_{24}$ alkenyl, non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, non-substituted $C_7$-$C_{24}$ aralkyl, substituted or non-substituted 3-10 member ring heterocyclyl, and heteroarylalkyl having an alkyl chain of 1 to 3 carbon atoms and a non-substituted aromatic heterocyclyl group with from 2 to 24 carbon atoms and from 1 to 3 atoms different from carbon or hydrogen.

4. The peptide according to claim 3, wherein $R^2$ is selected from the group consisting of —$NR^3R^4$ and —$OR^3$, wherein $R^3$ and $R^4$ are the same or different and are selected from the group consisting of H, methyl, ethyl, hexyl, dodecyl and hexadecyl.

5. The peptide according to claim 1, wherein $AA^1$ is -Glu-, $AA^2$ is -Met-, $AA^3$ is -Ala- and $AA^4$ is -Ile-.

6. The peptide according to claim 1, wherein $AA^1$ is -Arg-, $AA^2$ is -Ahx-, $AA^3$ is -Ala- and $AA^4$ is a single bond.

7. The peptide according to claim 1, wherein $AA^1$ is -Arg-, $AA^2$ is -Phg-, $AA^3$ is -Phg- and $AA^4$ is a single bond.

8. The peptide according to claim 1, wherein $R^1$ is H, acetyl, lauroyl, myristoyl or palmitoyl, $AA^1$ is -L-Glu-, $AA^2$ is -L-Met-, $AA^3$ is -L-Ala-, $AA^4$ is -L-Ile- and $R^2$ is —$NR^3R^4$ or —$OR^3$, wherein $R^3$ and $R^4$ are independently selected from the group consisting of H, methyl, ethyl, hexyl, dodecyl and hexadecyl.

9. The peptide according to claim 1, wherein $R^1$ is H, acetyl, lauroyl, myristoyl or palmitoyl, $AA^1$ is -L-Arg-, $AA^2$ is -Ahx-, $AA^3$ is -L-Ala-, $AA^4$ is a single bond and $R^2$ is —$NR^3R^4$ or —$OR^3$, wherein $R^3$ and $R^4$ are independently selected from the group consisting of H, methyl, ethyl, hexyl, dodecyl and hexadecyl.

10. The peptide according to claim 1, wherein $R^1$ is H, acetyl, lauroyl, myristoyl or palmitoyl, $AA^1$ is -L-Arg-, $AA^2$ is -L-Phg- or -D-Phg-, $AA^3$ is -L-Phg- or -D-Phg-, $AA^4$ is a single bond and $R^2$ is —$NR^3R^4$ or —$OR^3$, wherein $R^3$ and $R^4$ are independently selected from the group consisting of H, methyl, ethyl, hexyl, dodecyl and hexadecyl.

11. The peptide according to claim 1, selected from the group consisting of:

Ac-L-Arg-L-Phg-L-Phg-OH,
Ac-L-Arg-L-Phg-D-Phg-OH,
Ac-L-Arg-D-Phg-L-Phg-OH,
Ac-L-Arg-D-Phg-D-Phg-OH,
Ac-L-Glu-L-Phg-L-Ala-OH,
Ac-L-Glu-D-Phg-L-Ala-OH,
Ac-L-Arg-L-Phg-L-Ala-L-Ile-OH (Ac-SEQ ID No. 11-OH),
Ac-L-Arg-D-Phg-L-Ala-L-Ile-OH (Ac-SEQ ID No. 12-OH),
Ac-L-Arg-Ahx-L-Phg-L-Ile-OH (Ac-SEQ ID No. 13-OH),
Ac-L-Arg-Ahx-D-Phg-L-Ile-OH (Ac-SEQ ID No. 14-OH),
H-L-Glu-L-Met-L-Ala-L-Ile-OH (H-SEQ ID No. 3-OH),
Ac-L-Arg-L-Met-L-Phg-L-Ile-OH (Ac-SEQ ID No. 15-OH),
Ac-L-Arg-L-Met-D-Phg-L-Ile-OH (Ac-SEQ ID No. 16-OH),
Ac-L-Arg-L-Phg-L-Ala-OH,
Ac-L-Arg-D-Phg-L-Ala-OH,
Ac-L-Glu-L-Phg-L-Ala-L-Ile-OH (Ac-SEQ ID No. 17-OH),
Ac-L-Glu-D-Phg-L-Ala-L-Ile-OH (Ac-SEQ ID No. 18-OH),
Ac-L-Glu-L-Met-L-Phg-L-Ile-OH (Ac-SEQ ID No. 19-OH),
Ac-L-Glu-L-Met-D-Phg-L-Ile-OH (Ac-SEQ ID No. 20-OH),
Ac-L-Arg-Ahx-L-Ala-OH,
Ac-L-Arg-L-Phg-L-Phg-NH—$(CH_2)_{15}$—$CH_3$,
Ac-L-Arg-L-Phg-D-Phg-NH—$(CH_2)_{15}$—$CH_3$,
Ac-L-Arg-D-Phg-L-Phg-NH—$(CH_2)_{15}$—$CH_3$,
Ac-L-Arg-D-Phg-D-Phg-NH—$(CH_2)_{15}$—$CH_3$,
Palm-L-Glu-L-Met-L-Ala-L-Ile-$NH_2$ (Palm-SEQ ID No. 3-OH),
Ac-L-Arg-Ahx-L-Ala-L-Ile-OH (Ac-SEQ ID No. 7-OH),
Ac-L-Arg-L-Phg-L-Phg-L-Ile-OH (Ac-SEQ ID No. 21-OH),
Ac-L-Arg-L-Phg-D-Phg-L-Ile-OH (Ac-SEQ ID No. 22-OH),
Ac-L-Arg-D-Phg-L-Phg-L-Ile-OH (Ac-SEQ ID No. 23-OH),
Ac-L-Arg-D-Phg-D-Phg-L-Ile-OH (Ac-SEQ ID No. 24-OH),
Ac-L-Glu-L-Phg-L-Phg-L-Ile-OH (Ac-SEQ ID No. 25-OH),
Ac-L-Glu-L-Phg-D-Phg-L-Ile-OH (Ac-SEQ ID No. 26-OH),
Ac-L-Glu-D-Phg-L-Phg-L-Ile-OH (Ac-SEQ ID No. 27-OH),
Ac-L-Glu-D-Phg-D-Phg-L-Ile-OH (Ac-SEQ ID No. 28-OH),
Ac-L-Arg-L-Met-L-Ala-L-Ile-OH (Ac-SEQ ID No. 10-OH),
Ac-L-Glu-L-Met-L-Ala-L-Ile-OH (Ac-SEQ ID No. 3-OH), its mixtures, and
its cosmetically or pharmaceutically acceptable salts.

12. A process for obtaining a peptide of formula (I), its stereoisomers, mixtures thereof, or its cosmetically or pharmaceutically acceptable salts as defined in claim 1, comprising synthesizing the peptide in solid phase or in solution phase.

13. A cosmetic or pharmaceutical composition comprising a cosmetically or pharmaceutically effective amount of at least one peptide of formula (I), its stereoisomers, mixtures thereof or its cosmetically or pharmaceutically acceptable salts, as defined in claim 1, and at least one cosmetically or pharmaceutically acceptable excipient or adjuvant.

14. A method for the treatment, care and/or cleansing of the skin, mucosae, scalp and/or nails, comprising the administration of an effective amount of at least one peptide of formula (I), its stereoisomers, mixtures thereof or its cosmetically or pharmaceutically acceptable salts, as defined in claim 1.

15. The method according to claim 14, wherein the treatment, care and/or cleansing consists of the stimulation of the defenses of the skin, mucosae, scalp and/or nails.

16. The method according to claim 14, wherein the treatment, care and/or cleansing is performed by means of topical or transdermal application of the peptide, mixtures thereof, or its cosmetically or pharmaceutically acceptable salts.

17. The method according to claim 14, wherein the treatment and/or care maintain the homeostasis of the microbial flora of the skin, mucosae, scalp and/or nails.

18. The method according to claim 14 for the treatment, care and/or cleansing of conditions, disorders and/or pathologies of the skin, mucosae, scalp and/or nails resulting from microorganism proliferation or being at risk of microorganism proliferation.

19. The method according to claim 18, wherein said conditions, disorders and/or pathologies are selected from the group consisting of acne, eczema, atopic dermatitis, sensitive skin, papulopustular rosacea, bromhidrosis, seborrheic dermatitis, oily hair and/or scalp, dandruff, ophthalmologic infections, candidiasis, bacterial vaginosis, gingivitis, periodontitis and halitosis.

20. The cosmetic or pharmaceutical composition according to claim 13, wherein the peptide of formula (I), its stereoisomers, mixtures thereof or its cosmetically or pharmaceutically acceptable salts, is incorporated in a delivery system or in a cosmetically or pharmaceutically acceptable sustained release system selected from the group consisting of liposomes, millicapsules, microcapsules, nanocapsules, sponges, vesicles, micelles, millispheres, microspheres, nanospheres, lipospheres, microemulsions, nanoemulsions, milliparticles, microparticles, nanoparticles and solid lipid nanoparticles and/or is adsorbed on a cosmetically or pharmaceutically acceptable solid support or solid organic polymer selected from the group consisting of talc, bentonite, silica, starch and maltodextrin.

21. The cosmetic or pharmaceutical composition according to claim 13, wherein it is selected from the group consisting of creams, multiple emulsions, anhydrous compositions, aqueous dispersions, oils, milks, balsams, foams, lotions, gels, hydroalcoholic solutions, liniments, sera, soaps, shampoos, unguents, mousses, ointments, powders, bars, pencils, sprays, aerosols, capsules, gelatin capsules, tablets, sugar-coated tablets, granulated forms, chewing-gums, solutions, suspensions, emulsions, syrups, jellies and gelatin.

22. The cosmetic or pharmaceutical composition according to claim 13, wherein it is a product selected from the group consisting of concealers, makeup foundations, makeup removal lotions, makeup removal milks, eye shadows, lipsticks, lip glosses, lip protectors, powders, nail polishes, nail polish removal lotions, cuticle removal lotions, deodorants and antiperspirants.

23. The cosmetic or pharmaceutical composition according to claim 13, wherein the peptide of formula (I), its stereoisomers, mixtures thereof or its cosmetically or pharmaceutically acceptable salts, is incorporated in a fabric, a nonwoven fabric or a medical device.

24. The cosmetic or pharmaceutical composition according to claim 13, wherein it additionally comprises a cosmetically or pharmaceutically effective amount of at least one active agent selected from the group consisting of agents stimulating or inhibiting melanin synthesis, whitening or depigmenting agents, propigmentation agents, self-tanning agents, anti-aging agents, NO-synthase inhibiting agents, antioxidant agents, free radical-scavengers and/or anti-atmospheric pollution agents, anti-glycation agents, emulsifying agents, emollients, organic solvents, liquid propellants, skin conditioners, humectants, substances that retain moisture, alpha hydroxy acids, beta hydroxy acids, moisturizers, vitamins, pigments or colorants, dyes, gelling polymers, thickeners, surfactants, softeners, anti-wrinkle agents, agents capable of reducing or treating under-eye bags, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, agents stimulating collagen synthesis, agents stimulating elastin synthesis, agents stimulating decorin synthesis, agents stimulating laminin synthesis, agents stimulating defensin synthesis, agents stimulating chaperone synthesis, agents stimulating hyaluronic acid synthesis, agents stimulating the synthesis of lipids and components of the stratum corneum, agents stimulating angiogenesis, agents inhibiting collagen degradation, agents inhibiting elastin degradation, agents stimulating fibroblast proliferation, agents stimulating keratinocyte proliferation, agents stimulating keratinocyte differentiation, skin-relaxing agents, agents stimulating glycosaminoglycan synthesis, DNA repairing agents, DNA protecting agents, anti-itching agents, agents for the treatment of sensitive skin, firming agents, anti-stretch mark agents, astringent agents, agents regulating sebum production, agents stimulating lipolysis, anti-cellulite agents, agents stimulating healing, coadjuvant healing agents, cytokine growth factors, calming agents, anti-inflammatory agents, agents acting on capillary circulation and/or microcirculation, agents acting on cell metabolism, agents intended to improve the dermal-epidermal junction, preservatives, perfumes, chelating agents, plant extracts, essential oils, marine extracts, agents coming from a biofermentation process, mineral salts, cell extracts and sunscreens, or mixtures thereof.

\* \* \* \* \*